(12) United States Patent
Philtron et al.

(10) Patent No.: US 10,473,624 B2
(45) Date of Patent: Nov. 12, 2019

(54) SHEAR WAVE SENSORS FOR ACOUSTIC EMISSION AND HYBRID GUIDED WAVE TESTING

(71) Applicant: FBS, Inc., Bellefonte, PA (US)

(72) Inventors: Jason Philtron, State College, PA (US); Cody Borigo, Port Matilda, PA (US); Steven E. Owens, Bellefonte, PA (US); Russell Love, Port Matilda, PA (US)

(73) Assignee: FBS, Inc., Bellefonte, PA (US)

( * ) Notice: Subject to any disclaimer, the term of this patent is extended or adjusted under 35 U.S.C. 154(b) by 128 days.

(21) Appl. No.: 15/715,276

(22) Filed: Sep. 26, 2017

(65) Prior Publication Data

US 2018/0031525 A1 Feb. 1, 2018

Related U.S. Application Data

(63) Continuation-in-part of application No. 14/878,595, filed on Oct. 8, 2015, now Pat. No. 9,910,016.
(Continued)

(51) Int. Cl.
*G01N 29/26* (2006.01)
*G01N 29/07* (2006.01)
(Continued)

(52) U.S. Cl.
CPC ......... *G01N 29/043* (2013.01); *G01N 29/069* (2013.01); *G01N 29/07* (2013.01);
(Continued)

(58) Field of Classification Search
CPC .... G01N 29/043; G01N 29/069; G01N 29/07; G01N 29/11; G01N 29/2412;
(Continued)

(56) References Cited

U.S. PATENT DOCUMENTS 3,545,262 A 12/1970 Steele et al.
3,713,127 A 1/1973 Keledy et al.
(Continued)

OTHER PUBLICATIONS

Rose, J.L., Ultrasonic Guided Waves in Solid Media, Cambridge University Press, (2014): pp. 1-15, 76-106, 269-275, 294-322, 408-417.
(Continued)

*Primary Examiner* — Helen C Kwok
(74) *Attorney, Agent, or Firm* — Duane Morris LLP

(57) ABSTRACT

A system includes at least one circumferentially-polarized $d_{15}$ shear ring transducer and a controller electrically coupled to the at least one circumferentially-polarized $d_{15}$ shear ring transducer. The at least one circumferentially-polarized $d_{15}$ shear ring transducer is configured to be disposed on a structure and to detect at least one shear horizontal-type acoustic emission from damage to the structure. The controller includes a machine-readable storage medium and a processor in signal communication with the machine-readable storage medium. The processor is configured to store acoustic emission signal data in the machine-readable storage medium when a signal amplitude detected by the at least one circumferentially-polarized d15 shear ring transducer crosses a first threshold.

22 Claims, 29 Drawing Sheets

Related U.S. Application Data

(60) Provisional application No. 62/400,705, filed on Sep. 28, 2016, provisional application No. 62/064,211, filed on Oct. 15, 2014.

(51) Int. Cl.
  *G01N 29/34*  (2006.01)
  *G01N 29/06*  (2006.01)
  *G01N 29/04*  (2006.01)
  *G01N 29/14*  (2006.01)

(52) U.S. Cl.
  CPC .......... *G01N 29/14* (2013.01); *G01N 29/262* (2013.01); *G01N 29/343* (2013.01); *G01N 2291/011* (2013.01); *G01N 2291/015* (2013.01); *G01N 2291/0258* (2013.01); *G01N 2291/0422* (2013.01); *G01N 2291/0425* (2013.01); *G01N 2291/0427* (2013.01); *G01N 2291/2623* (2013.01); *G01N 2291/2626* (2013.01); *G01N 2291/2694* (2013.01)

(58) Field of Classification Search
  CPC .. G01N 29/262; G01N 29/343; G01N 29/348; G01N 29/2462; G01N 29/341; G01N 29/221
  See application file for complete search history.

(56) References Cited

U.S. PATENT DOCUMENTS

| | | | |
|---|---|---|---|
| 3,858,439 A | 1/1975 | Nakamura | |
| 4,009,463 A | 2/1977 | Vercellotti et al. | |
| 4,033,179 A | 7/1977 | Romrell | |
| 4,088,907 A | 5/1978 | Jones et al. | |
| 4,137,470 A | 1/1979 | Desormiere et al. | |
| 4,207,771 A | 6/1980 | Carlos et al. | |
| 4,592,034 A | 5/1986 | Sachse et al. | |
| 5,029,474 A | 7/1991 | Schulze | |
| 5,321,333 A * | 6/1994 | Walden | G01H 1/10 310/318 |
| 5,581,037 A | 12/1996 | Kwun et al. | |
| 5,714,687 A | 2/1998 | Dunegan | |
| 6,041,656 A | 3/2000 | Dunegan | |
| 6,119,804 A * | 9/2000 | Owen | G01V 1/047 181/113 |
| 6,360,608 B1 | 3/2002 | Dunegan | |
| 6,396,262 B2 * | 5/2002 | Light | G01N 17/006 324/220 |
| 6,996,480 B2 | 2/2006 | Giurgiutiu et al. | |
| 8,217,554 B2 * | 7/2012 | Royer, Jr. | B64D 15/00 244/134 A |
| 8,907,665 B2 | 12/2014 | Rose et al. | |
| 9,638,671 B2 * | 5/2017 | Borigo | G01N 29/2412 |
| 9,910,016 B2 * | 3/2018 | Borigo | G01N 29/043 |
| 2010/0217544 A1 * | 8/2010 | Yan | G01N 29/07 702/56 |
| 2011/0203375 A1 * | 8/2011 | Farthing | G01N 29/07 73/628 |
| 2011/0239785 A1 * | 10/2011 | Ting | G01L 3/10 73/862.325 |
| 2013/0327148 A1 * | 12/2013 | Yan | G01N 29/34 73/628 |
| 2015/0053009 A1 * | 2/2015 | Yan | G01N 29/07 73/598 |
| 2015/0073729 A1 * | 3/2015 | Borigo | G01N 29/2412 702/39 |
| 2017/0205374 A1 * | 7/2017 | Koehler | B06B 1/06 |

OTHER PUBLICATIONS

Trémolet de Lacheisserie, E., Magnetostriction: Theory and Applications of Magnetoelasticity, CRC press, (1993), pp. 198, 339-352, 359-361.

Kuokkala, V.T. and Schwarz, R.B., "The use of magnetostrictive film transducers in the measurement of elastic moduli and ultrasonic attenuation of solids," Rev. Sci. Instrum., 63(5), pp. 3136-3142, 1992.

Joule, J.P., "On the effects of magnetism upon the dimensions of iron and steel bars," Phil. Mag., Series 3, 30(199), pp. 76-87, 1842.

* cited by examiner

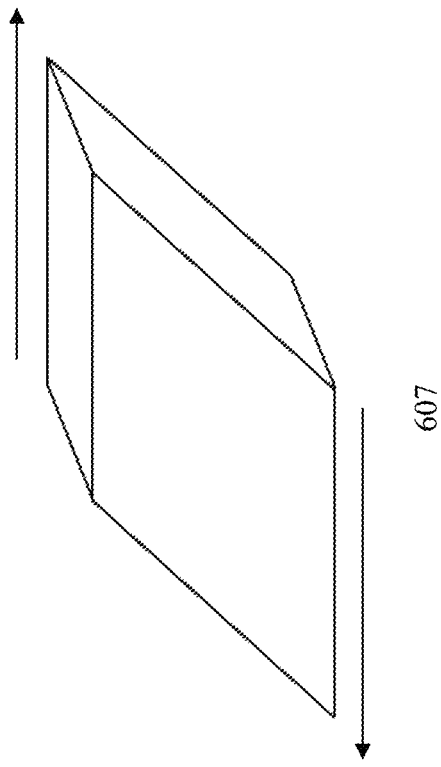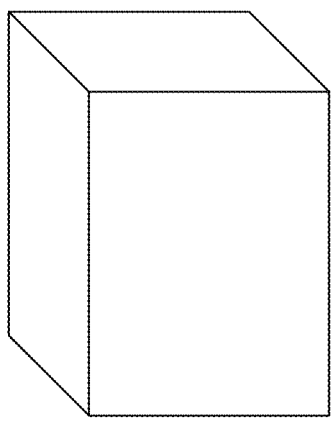
FIG. 6B

SHEAR WAVE SENSORS FOR ACOUSTIC EMISSION AND HYBRID GUIDED WAVE TESTING

CROSS-REFERENCE TO RELATED APPLICATIONS

This application claims priority to U.S. Provisional Patent Application No. 62/400,705, filed Sep. 28, 2016, and is a continuation-in-part of U.S. patent application Ser. No. 14/878,595, filed Oct. 8, 2015, which claims priority to U.S. Provisional Patent Application No. 62/064,211, filed Oct. 15, 2014, the entireties of which are herein incorporated by reference.

FIELD OF DISCLOSURE

The disclosed systems and methods relate to structural health monitoring and non-destructive examination. More specifically, the disclosed systems and methods relate to structural heath monitoring and non-destructive examination of plates and plate-like structures, rods, beams and bars, rail, storage tanks and pressure vessels, tubes and pipes, bridges, and other structures.

BACKGROUND

Various systems and methods exist for structural heath monitoring ("SHM") of structures using acoustic emission ("AE"). However, these systems and monitoring techniques typically use disk-shaped $d_{33}/d_{13}$-type piezoelectric transducers that are resonant in a thickness or radial mode. These sensors are susceptible to environmental noise, such as rain and wind-blown sand and dirt, and have localization algorithms which rely on velocities of mode(s) which vary depending on the structure's thickness and the frequency of the AE event, causing errors in event localization. The use of an AE sensor that is primarily sensitive to a shear-type guided wave mode can reduce unwanted environmental noise as well as increase the robustness of localization algorithms, among other benefits. Additionally, a sensor which can perform active guided wave ("GW") sensing, as well as passive AE sensing, can combine the advantages of both inspection methods.

SUMMARY

In some embodiments, a system includes at least one circumferentially-polarized $d_{15}$ shear ring transducer and a controller electrically coupled to the at least one circumferentially-polarized $d_{15}$ shear ring transducer. The at least one circumferentially-polarized $d_{15}$ shear ring transducer is configured to be disposed on a structure and to detect at least one shear horizontal-type acoustic emission from damage to the structure. The controller includes a machine-readable storage medium and a processor in signal communication with the machine-readable storage medium. The processor is configured to store acoustic emission signal data in the machine-readable storage medium when a signal amplitude detected by the at least one circumferentially-polarized $d_{15}$ shear ring transducer crosses a first threshold.

In some embodiments, a system includes a plurality of transducers configured to be disposed on a structure and a controller electrically coupled to the plurality of transducers. The controller includes a machine-readable storage medium and a processor in signal communication with the machine-readable storage medium. The processor configured to store acoustic emission signal data in the machine-readable storage medium when a signal amplitude detected by at least one of the plurality of transducers crosses a threshold, cause a pulse generator to pulse at least one of the plurality of transducers to transmit ultrasonic guided wave energy in the structure, process at least one guided wave signal resulting from said transmitted ultrasonic guided wave energy to identify at least one of a presence, a location, or a severity of at least one defect in the structure, and store the at least one guided wave signal in the machine-readable storage medium.

In some embodiments, a method includes detecting, using a processor and a plurality of circumferentially-polarized $d_{15}$ shear ring transducers disposed on a structure, a shear horizontal-type acoustic emission in a first frequency band in the structure. The shear horizontal-type acoustic emission signal data is stored in a machine-readable storage medium when an amplitude of the shear horizontal-type acoustic emission detected by at least one of the plurality of circumferentially-polarized $d_{15}$ shear ring transducers crosses a first threshold, and the processor is used to calculate a location of a source of the acoustic emission in said structure using a source location algorithm, a velocity of the shear horizontal-type acoustic emission in the structure, and the acoustic emission signal data.

BRIEF DESCRIPTION OF THE DRAWINGS

FIG. 6B illustrates the deformation mode of a piezoelectric $d_{15}$ shear block element.

DETAILED DESCRIPTION

Figure 1:
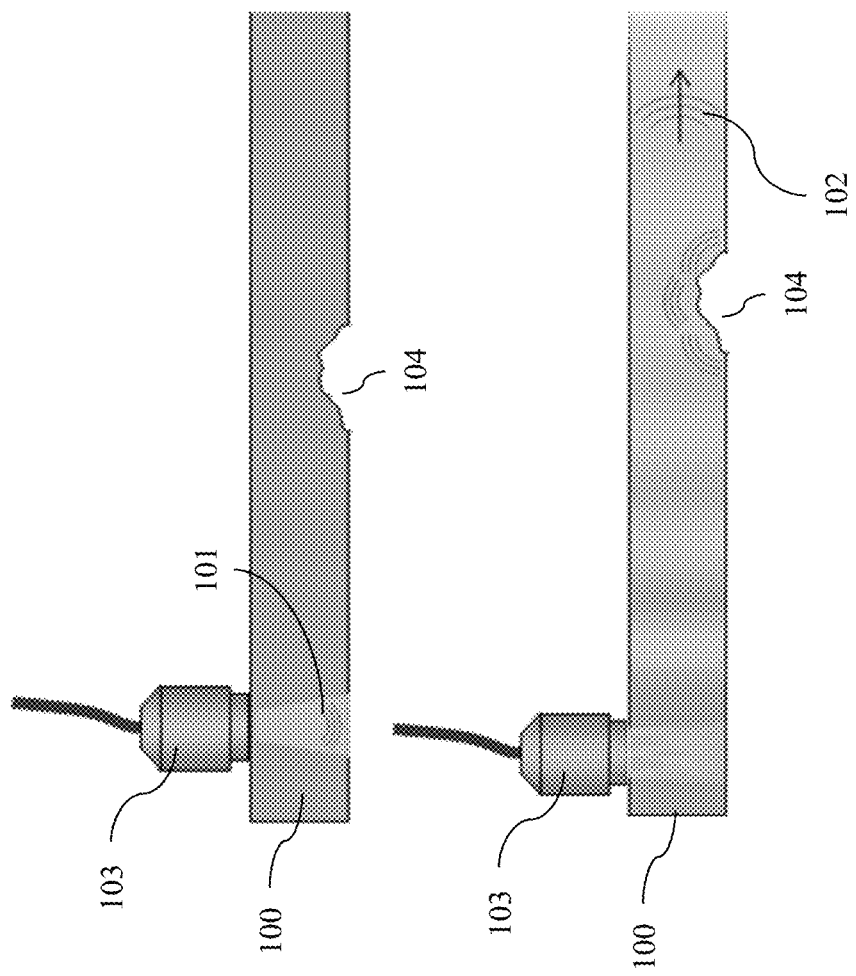
FIG. 1 illustrates the concept of guided waves in a plate-like structure and compares them to bulk waves.

This description of the exemplary embodiments is intended to be read in connection with the accompanying drawings, which are to be considered part of the entire written description.

Circumferentially-polarized piezoelectric $d_{15}$ shear ring elements are utilized to generate and detect shear horizontal-type guided waves in plate-like structures to perform at least one of non-destructive evaluation and structural health monitoring of said plate-like structures where acoustic emission ("AE") is understood to be an inspection technique categorized within these methods. The omnidirectional shear horizontal ("SH") wave generation/reception and sensitivity characteristics of the circumferentially-polarized piezoelectric $d_{15}$ shear ring elements yields superior AE results in many embodiments when compared to conventional disk-type $d_{33}/d_{13}$ piezoelectric sensors, which are primarily sensitive to Lamb-type guided wave modes.

In some embodiments, at least one shear ring element is coupled to a structure to generate SH guided waves in all directions in said structure. The at least one ring element may also be coupled to the structure to detect SH guided waves impinging on the element location from any direction. These waves may have been generated by the at least one ring element, by another element, or by an AE event such as an impact, crack growth, or active corrosion, and may also be reflections from a defect.

In some embodiments, a plurality of shear ring elements is coupled to a structure in an array around a perimeter of an area to be monitored using acoustic emission. Acoustic emission events generate SH wave signals which are received by at least one shear ring element in the array, and a damage localization algorithm, which triangulates the origin of the AE event based on wave velocity, time delay between received signals, and known geometry of the sensor array, is used to map each AE event to a location on the structure.

Additional methods for source location can also be implemented. One example of another method for source location is synthetic focusing back-propagation algorithms used in pipes and plates, such as those described in Rose, J. L., Ultrasonic Guided Waves in Solid Media, Cambridge University Press, New York, N.Y., 2014, the entirety of which is incorporated by reference herein.

In some embodiments, at least one magnetostrictive transducer in shear horizontal wave mode, or another shear-sensitive transducer type, is substituted for at least one shear ring element to generate or receive guided waves in a structure singly or as part of a plurality of elements in an array.

Acoustic emission ("AE") is a passive inspection technique categorized within the fields of non-destructive evaluation and structural health monitoring where resonant transducers are used to "listen" to noises produced by a structure that indicate damage. In practice, two or more AE sensors are typically placed in an array around the area of interest. Damage mechanisms, such as cracking, active corrosion, fiber breakage and delamination, among other types, typically produce a release of energy. This energy travels through the structure as a stress wave. In many structures, these acoustic waves travel as ultrasonic guided waves ("GWs") of three main mode types: symmetric (S), antisymmetric (A), and shear horizontal (SH). Each GW mode has a unique velocity and other characteristics which are dependent on the structure's material properties, thickness, and the frequency of the wave energy. Typically, AE sensors are used in a frequency range in which the three fundamental modes ($S_0$, $A_0$, and $SH_0$) are dominant.

Conventional AE sensors use $d_{33}/d_{13}$ type piezoelectric disks that are sensitive to a thickness resonance and/or a radial resonance. These two motions match the displacements produced by the fundamental antisymmetric ($A_0$) and symmetric ($S_0$) modes at low frequency at the surface of a plate-like structure. For this reason, conventional AE sensors are primarily sensitive to Lamb-type GW modes. Conventional AE sensors are typically not very sensitive to wave energy in the fundamental shear horizontal ($SH_0$) mode. However, many AE damage mechanisms produce energy in all three fundamental modes.

Although conventional AE sensors work very well in a variety of situations, there are several issues that, when addressed, would allow for a wider range of AE applications and more accurate and robust data collection. Many of these issues can be resolved by utilizing shear-type AE sensors, particularly shear-type sensors that could also be used in an active guided wave mode. Several issues with conventional AE sensors include high sensitivity to environmental noise, AE event localization errors due to source mode content changes and attenuation, and AE event localization errors due to thickness variations in the structure. These issues can be resolved or greatly reduced by using shear-sensitive sensors. Additionally, conventional AE sensors only measure damage progression, but cannot directly detect damage state. The use of a shear-type sensor that can also function as an active GW sender will be able to directly assess the damage state. The following description describes how to use shear-type sensors that are sensitive to the $SH_0$ mode for AE testing and the many benefits that are derived from them.

Guided waves are formed from the constructive interference of ultrasonic bulk waves that have interacted with the boundaries of the structure in which they propagate. A conceptual illustration of this concept is provided in FIG. 1, in which bulk waves 101 and guided waves 102 are shown being generated in an identical plate-like structure 100 using ultrasonic transducers 103. Guided waves are unique in the sense that they are capable of propagating for long distances compared to conventional ultrasonic waves and can be used to inspect hidden/inaccessible structures like buried or cased piping, plates behind walls or insulation, etc., which allows them to detect corrosion 104 or other defects from remote locations. Unlike "spot-checking" with conventional ultrasonic techniques, guided waves are able to provide up to 100% volumetric inspection. Furthermore, guided waves provide an efficient and cost-effective means of inspection due to increased inspection speed and simplicity, particularly for large structures that would require a large number of ultrasonic bulk wave spot-check measurements as described in Rose, J. L., Ultrasonic Guided Waves in Solid Media, Cambridge University Press, New York, N.Y., 2014.

Figure 2:
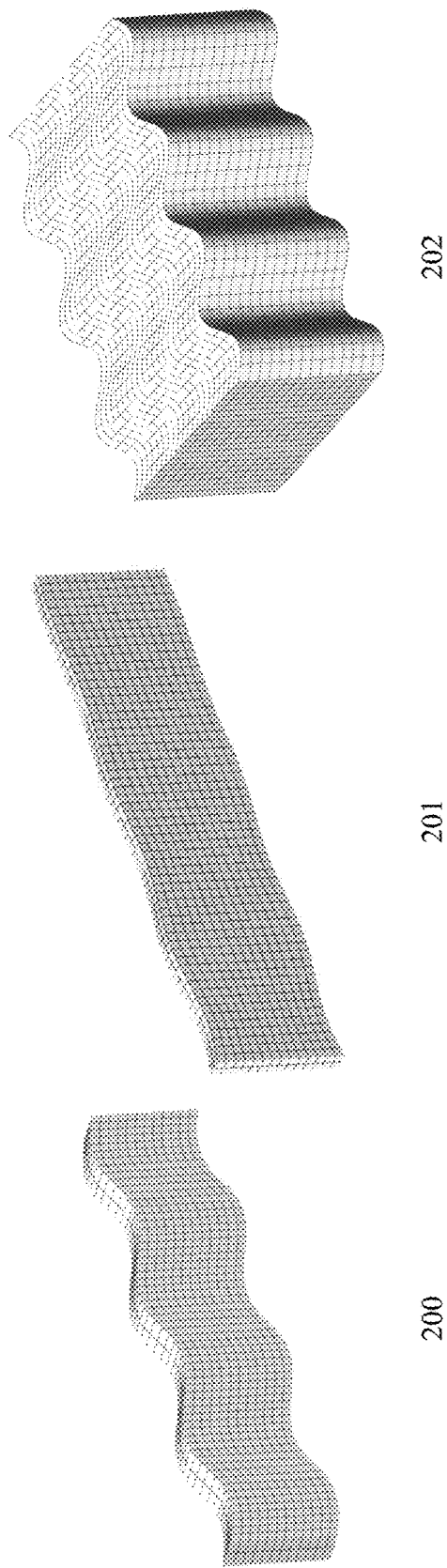
FIG. 2 illustrates the vibration of Lamb-type and SH-type guided waves in a structure.

In plates and plate-like structures, i.e. structures whose radius of curvature is much greater than their thickness, there are two primary types of guided wave modes that can be excited: Lamb and shear horizontal (SH). The general propagation characteristics of these two mode types are illustrated in FIG. 2, which illustrates a cross-sectional view of a solid plate under deformation induced by an $A_0$ Lamb wave 200, an $S_0$ Lamb wave 201, and an SH wave 202. In some embodiments, SH-type waves, which have the defining characteristic of generating only in-plane lateral vibration as they propagate through a structure, are used. On the other hand, Lamb-type waves generate out-of-plane vibration and in-plane vibration parallel to the wave propagation direction as described in Rose, J. L., Ultrasonic Guided Waves in Solid Media, Cambridge University Press, New York, N.Y., 2014.

Figure 3:
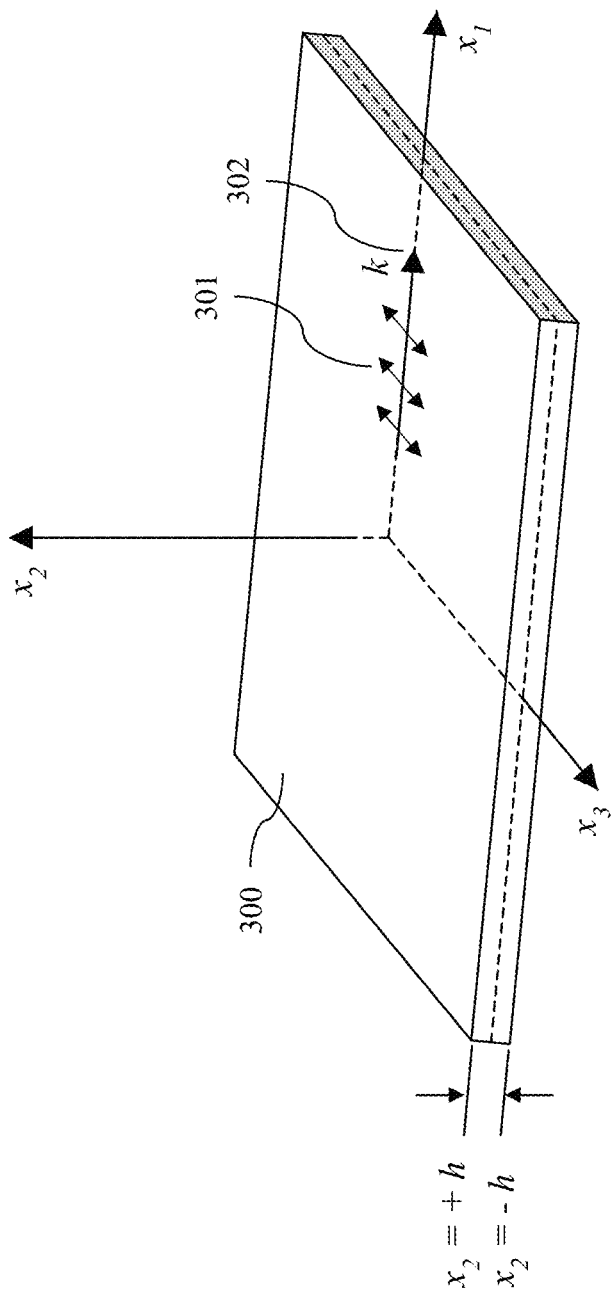
FIG. 3 illustrates the vibration components and propagation direction of SH-type guided waves in a structure.

FIG. 3 illustrates the concept of SH-type waves having in-plane lateral vibration 301 that are perpendicular to the wave propagation direction 302 in a plate 300. The terms "Lamb wave" and "SH wave" can be strictly defined as these types of guided waves in homogenous, linear, isotropic plates having constant thickness. However, for the purposes of this disclosure, the terms "Lamb wave" and "SH wave" will be more broadly used to describe any of the Lamb-type and SH-type waves in plate-like structures that closely match the characteristics of the waves described by these strict definitions, including plates with a small degree of curvature and anisotropic plates.

Figure 4:
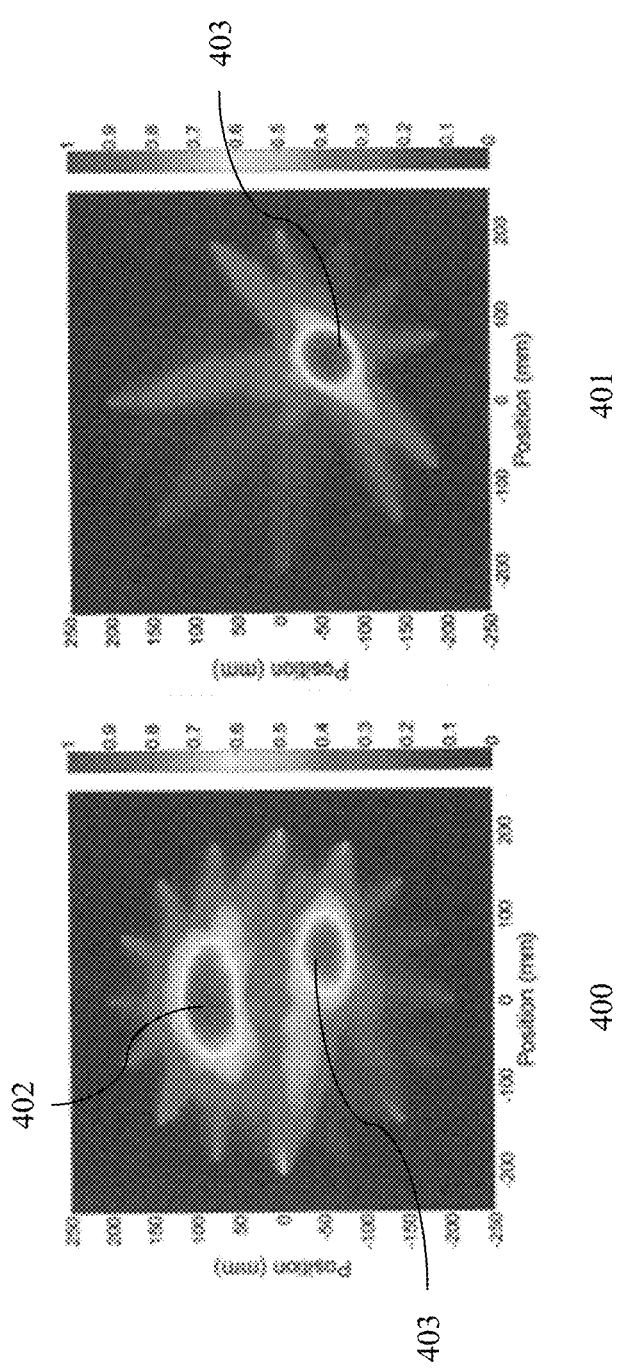
FIG. 4 illustrates guided wave CT images generated with a fluid-sensitive guided wave mode and a fluid-insensitive guided wave mode.

The unique pure shear characteristic of SH waves makes them particularly useful for many non-destructive evaluation (NDE) and structural health monitoring (SHM) applications. For instance, SH waves are insensitive to the presence of inviscid liquids, which means that they are not attenuated by fluid-loaded boundary conditions of a structure such as a fluid-filled pipe, a ship hull with fluid on one side, or a submerged plate. Additionally, this insensitivity to fluids also means that SH wave measurements collected on a structure with and without fluid loading are practically identical, which is useful for the purposes of SHM wherein guided wave signals are compared over time and sensitivity to environmental conditions like rain or fluid-loading are undesirable. One example of the advantage to insensitivity to fluids is shown in FIG. 4, wherein a first computed tomogram (CT) image 400 was generated using a guided wave mode that is sensitive to fluid loading and a second CT image 401 was generated using guided wave modes that are insensitive to fluid loading. The guided wave system used to generate image 400 was unable to distinguish the corrosion defect 403 and the surface liquid 402, while the system designed to utilize fluid-insensitive guided wave modes only detects the corrosion defect 403.

Figure 5:
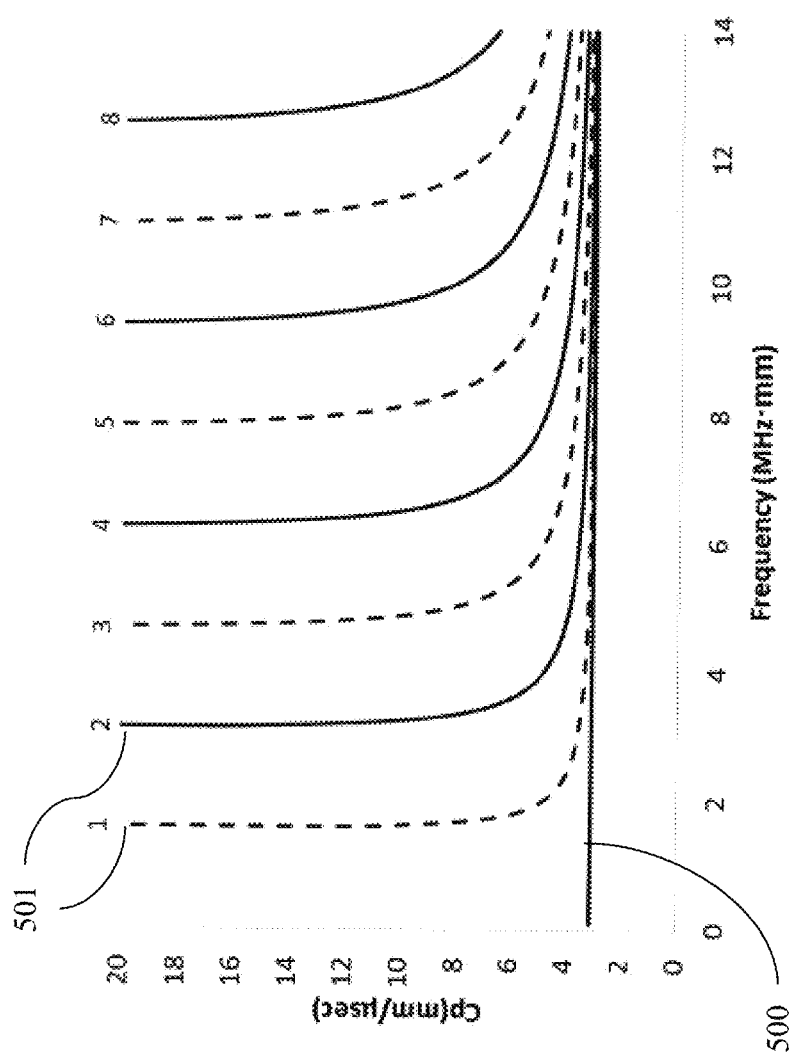
FIG. 5 illustrates the dispersion curves for SH wave modes in an isotropic plate-like structure.

SH waves also have the advantage of generally having simpler propagation characteristics than Lamb waves, particularly with respect to their velocity characteristics and the reduced number of higher order modes. Dispersion curves for SH wave modes in an isotropic plate are provided as one example in FIG. 5. Here it is apparent that the fundamental $SH_0$ mode 500 is strictly nondispersive, i.e., the velocity is independent of frequency, which can be highly advantageous for NDE and SHM due to the simplicity of processing the guided wave data collected with such a mode. There are also fewer higher-order guided wave modes 501 at any given frequency than for Lamb waves in a comparable structure, which can make signal interpretation and system design simpler.

Figure 6A:
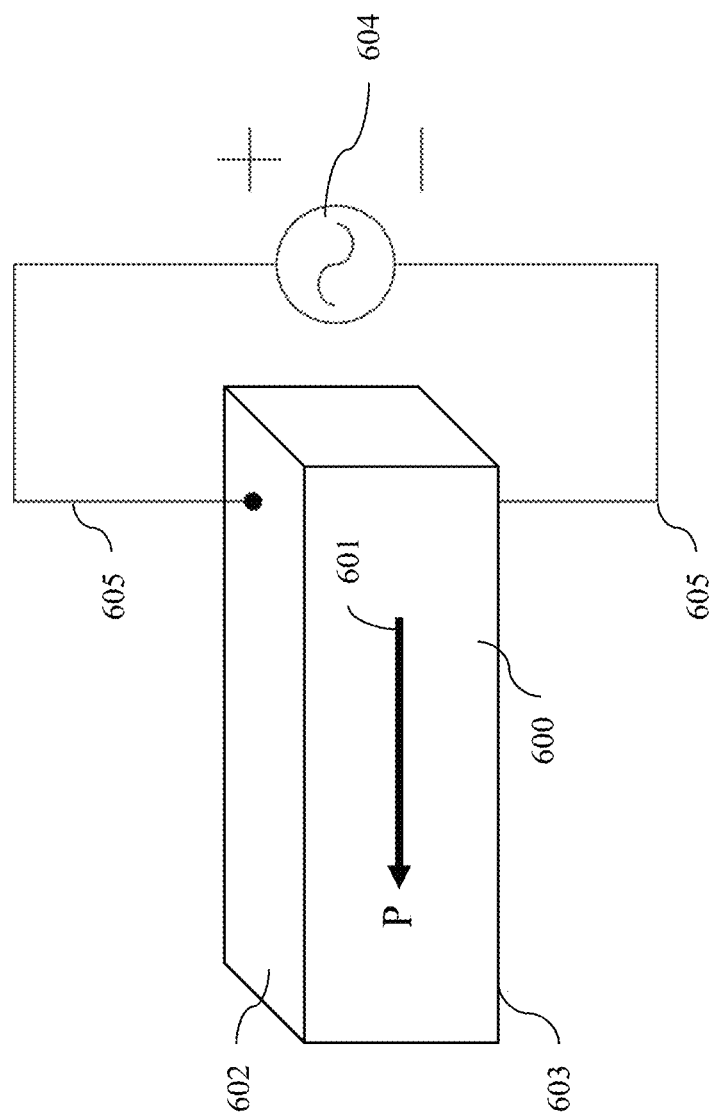
FIG. 6A illustrates a piezoelectric $d_{15}$ shear block element.

Piezoelectric transducers can be used to generate and to detect guided waves for the purposes of NDE and SHM. To generate SH waves in a structure, the $d_{15}$ piezoelectric coefficient can be employed in shear block element transducers, such as the shear block element illustrated in FIG. 6A. Here the piezoceramic block element 600 is polarized in the direction indicated by the arrow 601, and an electric potential is applied across the electrode faces 602 and 603 using the alternating voltage source 604 attached with leads 605. FIG. 6B illustrates one example of deformation experienced by a shear $d_{15}$ piezoceramic block when a voltage is applied. Specifically, reference numeral 606 corresponds to an undeformed shear $d_{15}$ piezoelectric block element, and reference numeral 607 corresponds to a shear $d_{15}$ piezoelectric block element in a deformed state. When the base of such an element is coupled to a structure using a rigid bond or viscous couplant, these shear vibrations are transmitted to the structure and SH guided waves can be generated. Conversely, impinging SH waves can also be detected by said transducers by inverse effect.

Figure 7A:
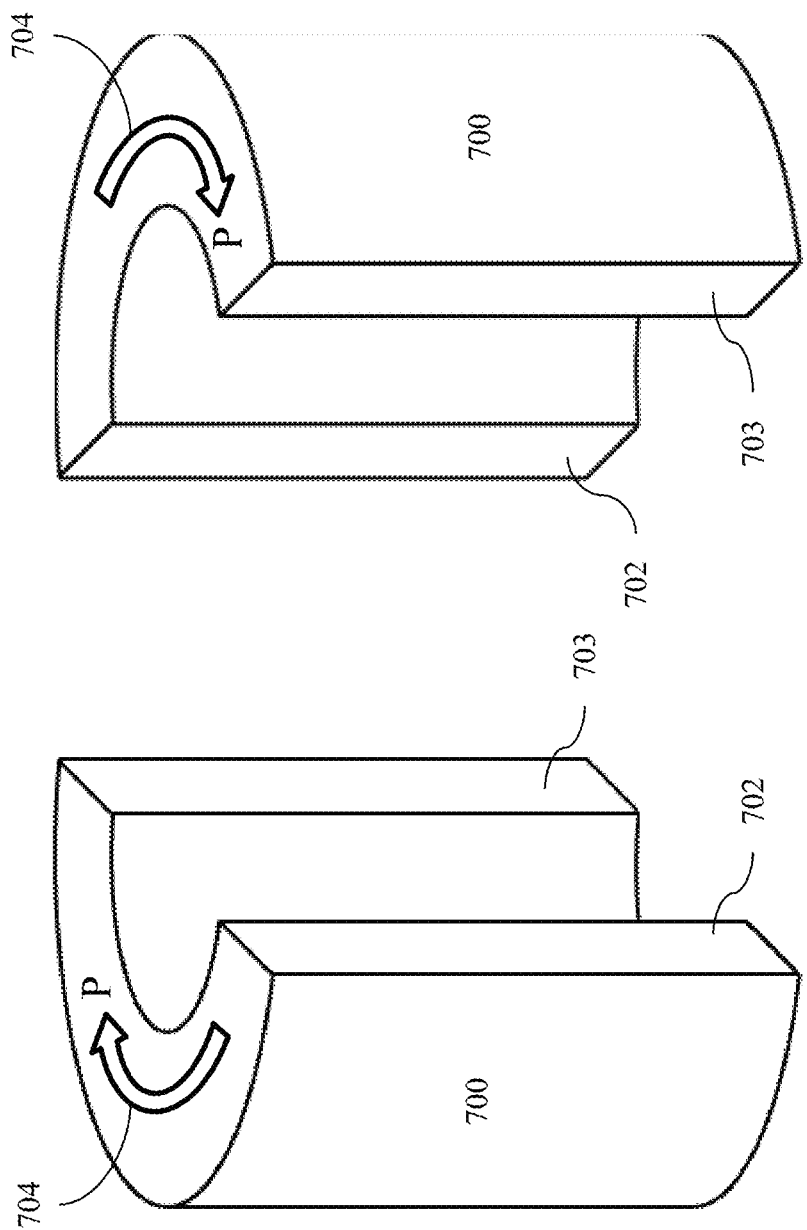
FIG. 7A illustrates the poling and assembly process of a circumferentially-poled piezoelectric d15 shear ring element.
Figure 7B:
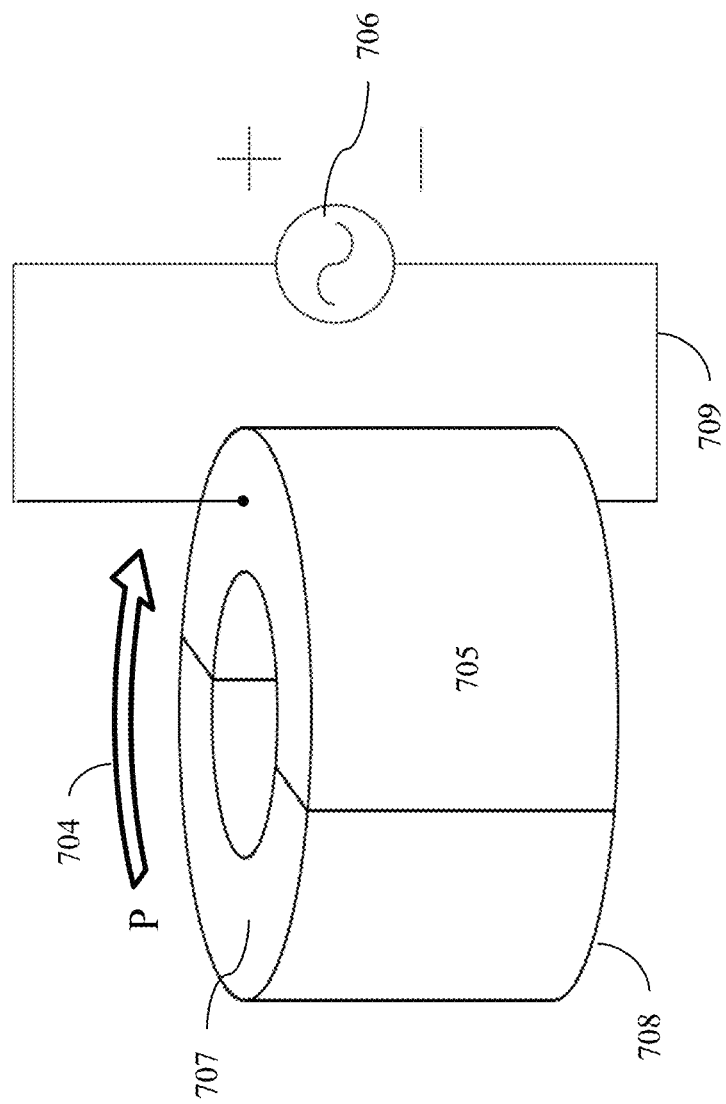
FIG. 7B illustrates a circumferentially-poled piezoelectric $d_{15}$ shear ring element.
Figure 7C:
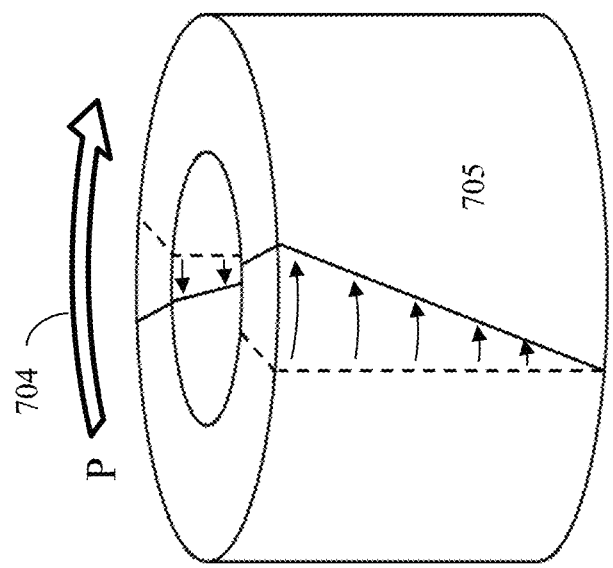
FIG. 7C illustrates the deformation mode of a circumferentially-poled piezoelectric $d_{15}$ shear ring element.

Another type of shear piezoelectric element is the circumferentially-polarized $d_{15}$ shear piezoelectric ring element that is illustrated in FIGS. 7A and 7B. The shear ring element is fabricated from two half rings 700 that are polarized quasi-circumferentially, in accordance with arrows 704, by applying high-voltage DC to the two vertical faces 702 and 703 (FIG. 7A) while the temperature of the element is greater than the Curie temperature. These half rings 700 are subsequently bonded together to form a full ring element 705, which can be excited with voltage source 706 applied to the upper and lower electrode surfaces 707 and 708 via leads 709 as shown in FIG. 7B. Note the rings can be split into thirds, quarters, and other numbers, as well as polygon-shaped ring segments to make poling and assembly easier are also possible configurations. The torsional vibration mode of the shear ring element is illustrated in FIG. 7C. This torsional deformation effectively excites SH guided waves omnidirectionally when coupled to a plate-like structure. The inner and outer radii, the thickness, and the piezoceramic material selected for the rings can all be adjusted to suit the specific requirements of the application as will be understood by people of ordinary skill in the art.

Additional variations upon this transducer design are also possible, and the specific embodiment detailed herein is non-limiting and used as one example of an omnidirectional piezoelectric $d_{15}$ shear ring element for SH-type guided wave generation in accordance with some embodiments. Additional embodiments may include shear rings that are fabricated from more than two segments, shear rings that are poled through the radius instead of the thickness dimension, and shear rings that are polygonal instead of truly circular.

Figure 8A:
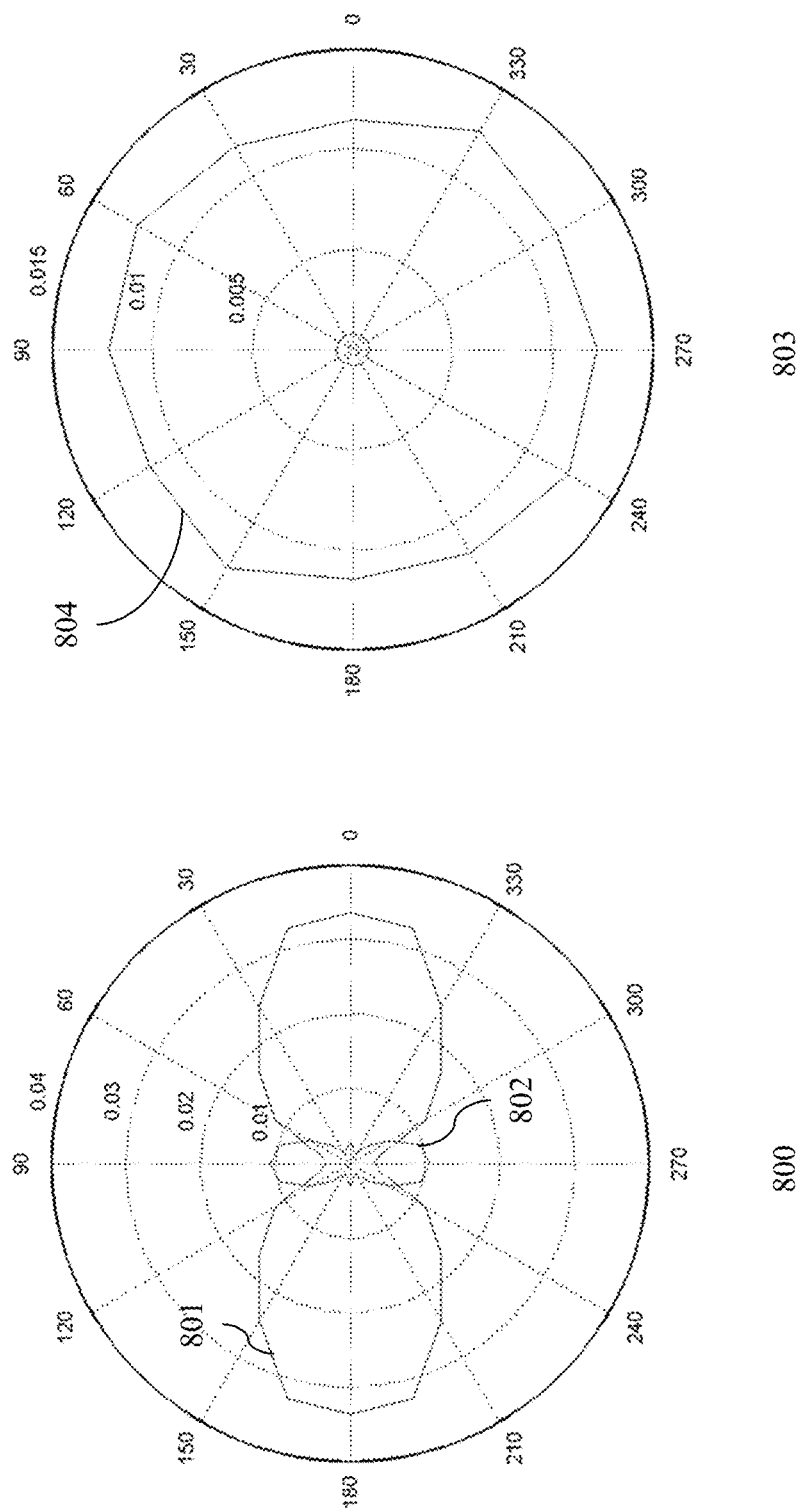
FIG. 8A illustrates the guided wave mode directionality of a piezoelectric $d_{15}$ shear block element and a circumferentially-poled piezoelectric $d_{15}$ shear ring element.
Figure 8B:
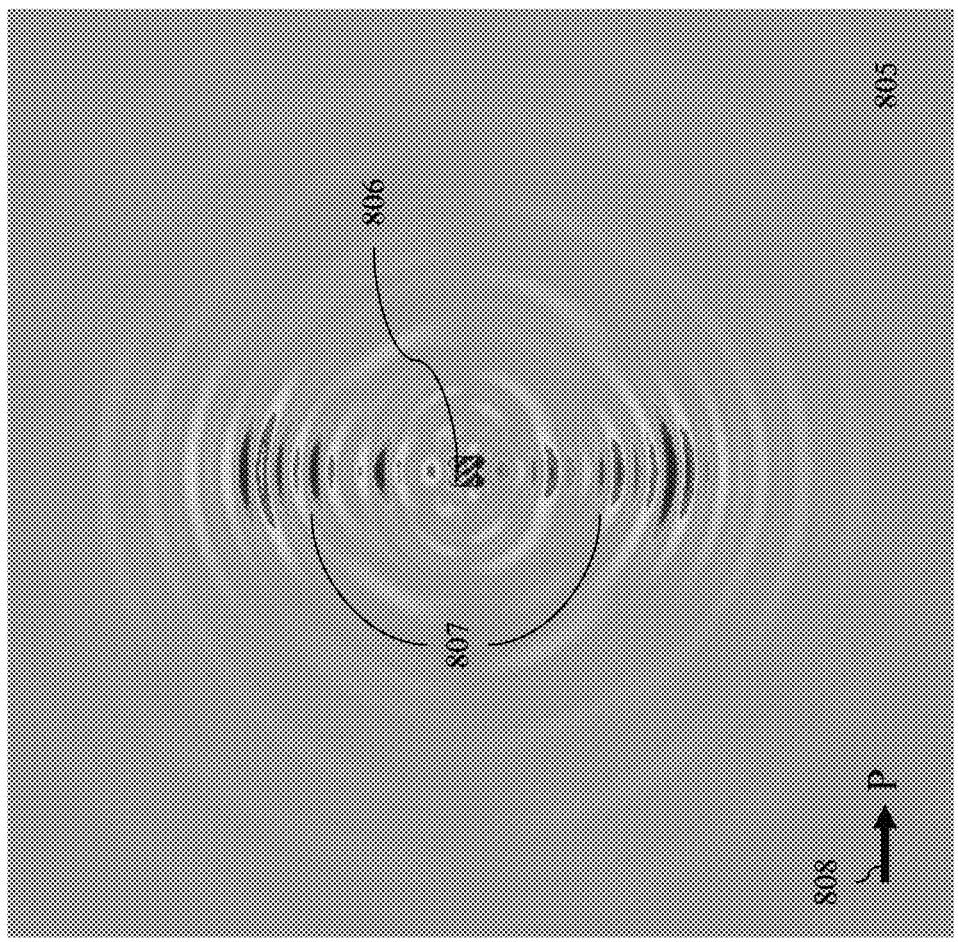
FIG. 8B illustrates the stress field output from a finite element model of a piezoelectric $d_{15}$ shear block element.

Shear $d_{15}$ piezoceramic block elements are highly directional in terms of SH wave excitation and sensitivity. This is illustrated by the experimental results provided in FIG. 8A, wherein the amplitude of the $SH_0$ and $S_0$ guided wave modes were recorded as a function of angle relative to a small $d_{15}$ piezoelectric shear block and a circumferentially-polarized $d_{15}$ shear ring in polar plots 800 and 803, respectively. In the polar plot 800 corresponding to the shear block element, it is apparent that the $SH_0$ amplitude 801 is maximized at 0° and 180° and nearly zero at 90° and 270°. The $S_0$ wave amplitude 802 generated by these blocks is maximized at 90° and 270° and nearly zero at 0° and 180°. This high degree of directionality is undesirable in many cases. Alternatively, the polar plot 803 corresponding to the shear ring element shows that the $SH_0$ amplitude 804 is nearly equivalent in all directions, which can be highly advantageous in many cases. The directionality of the $d_{15}$ shear block elements is also illustrated in FIG. 8B, which is a shear stress field output from a finite element model of a plate 805 induced by shear block element 806, which is polarized in the direction indicated by 808. The high degree of directionality is apparent by the beams of $SH_0$ guided wave energy 807 emitted by the element. In this respect, the shear ring element is superior to the shear block element for many guided wave applications due to the ability of the shear ring to transmit guided wave energy omnidirectionally into a structure and to detect guided wave energy incident upon it from any direction in a structure.

A circumferentially-polarized $d_{15}$ shear ring element has sensitivity to shear horizontal-type guided wave modes in at least one first frequency band and, in some embodiments, has sensitivity to Lamb-type guided wave modes in at least one second frequency band. The ability to have sensitivity to various types of guided wave modes in multiple frequency bands is due to the complex resonant vibration modes of the element design and/or its interaction with its housing. Therefore, it is possible with a single shear ring element to detect and distinguish between both shear horizontal-type and Lamb-type acoustic emission signal data.

Figure 9A:
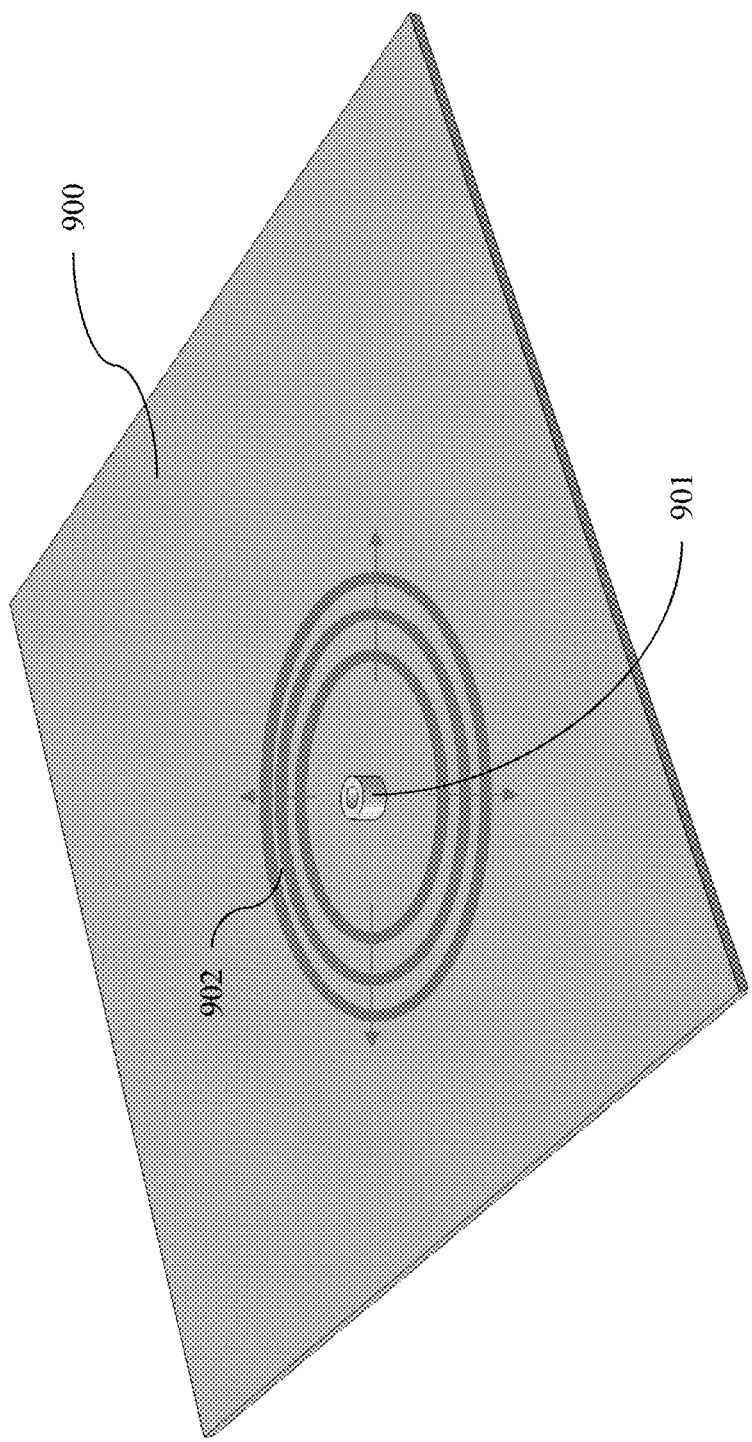
FIG. 9A illustrates a shear ring element coupled to and generating SH guided waves in a plate-like structure.
Figure 9B:
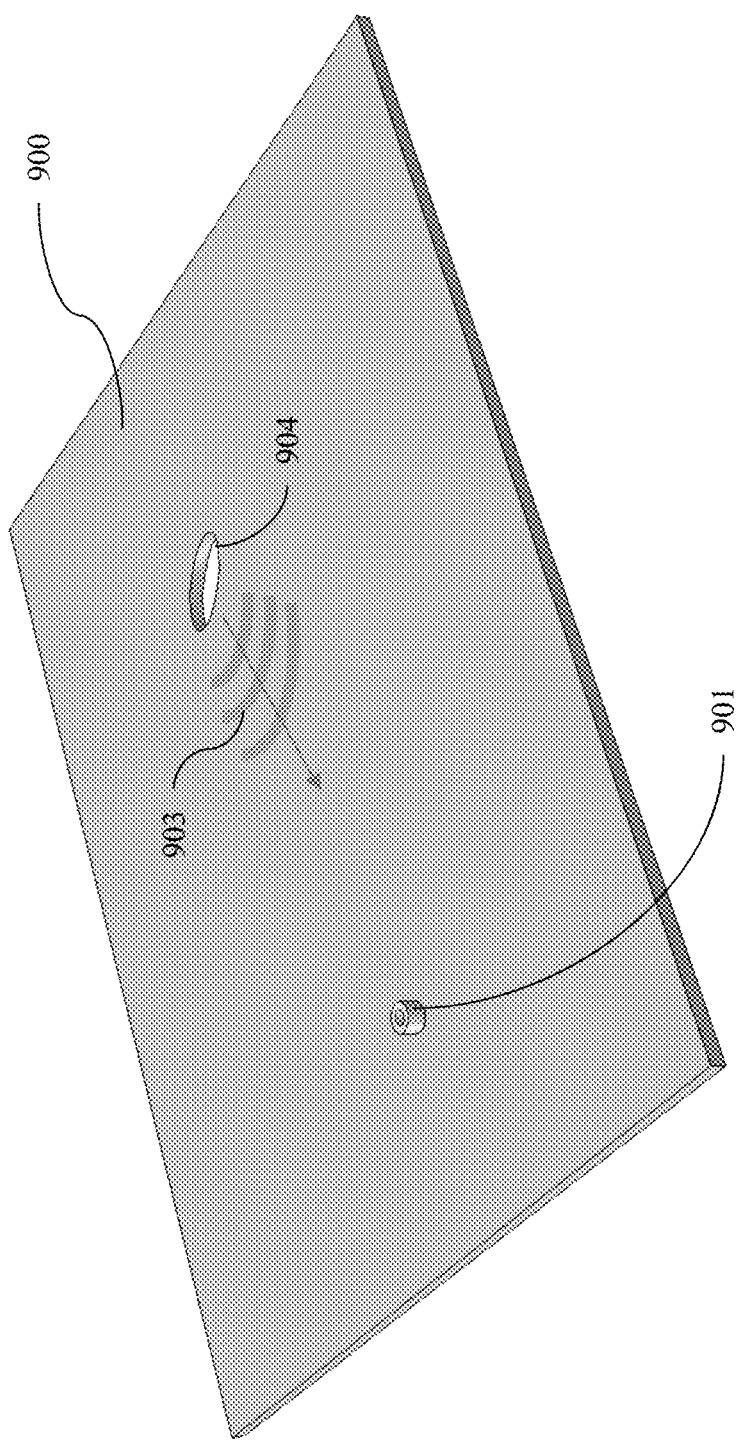
FIG. 9B illustrates a shear ring element coupled to and detecting SH guided waves in a plate-like structure.
Figure 9C:
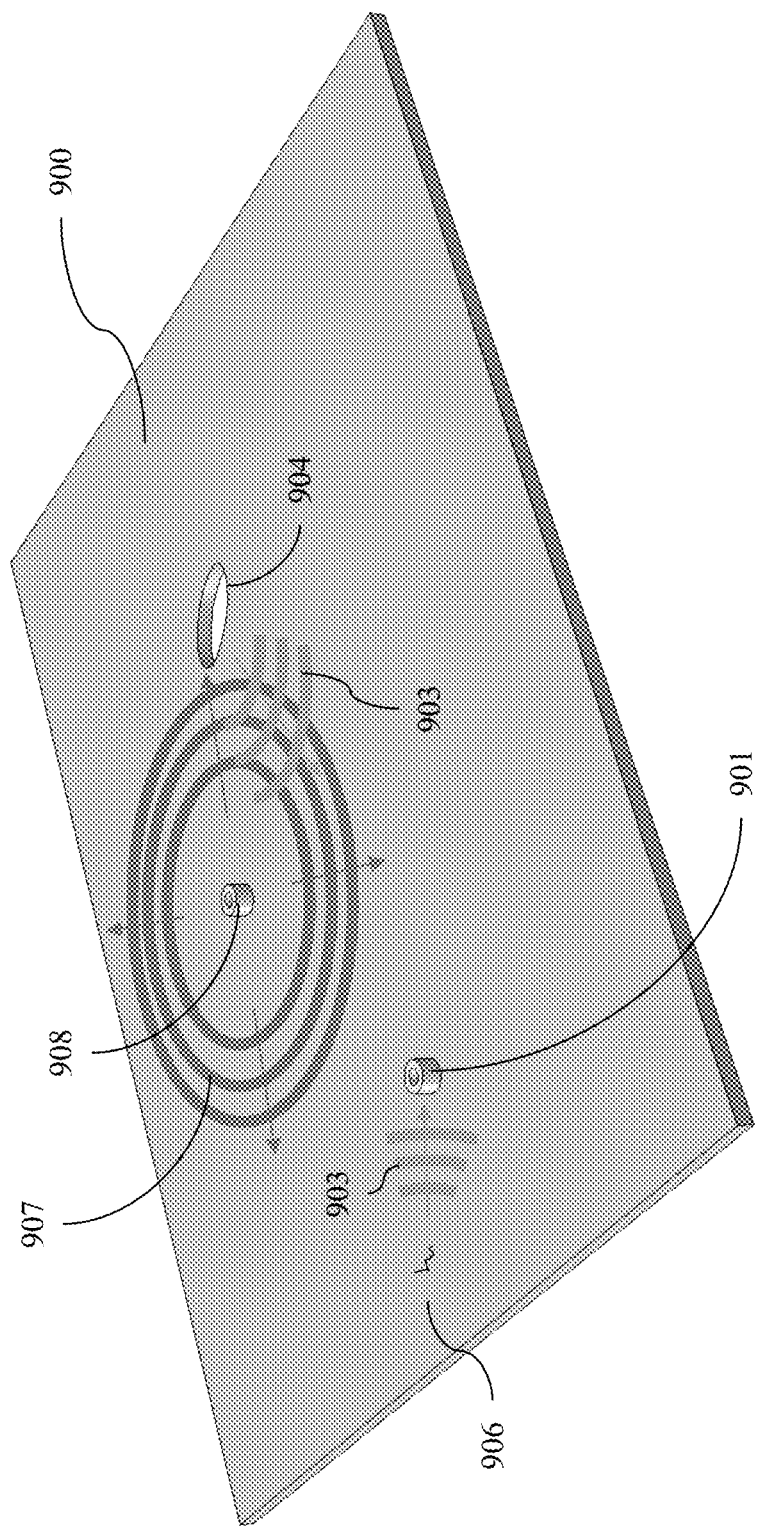
FIG. 9C illustrates two shear ring elements coupled to, and generating and detecting SH guided waves that are interacting with various defects in, a plate-like structure.

FIGS. 9A-9C illustrate the various ways in which shear ring elements can be used to transmit and/or receive guided wave energy omnidirectionally. For example, in FIG. 9A, a ring element 901 is shown generating guided waves 902 omnidirectionally in structure 900. The at least one ring element 901 may also be coupled to the structure to detect SH guided waves 903 impinging on the element location from any direction as shown in FIG. 9B. FIG. 9C illustrates waves 907 and 903 generated by shear ring element 901 or by another element 908 or energy source such as an impact or crack growth 906 and may also be reflections 903 from a defect such as a crack 906, a delamination, corrosion, or a hole 904.

In some embodiments, the shear ring element will be mounted on a wear plate and packaged in a transducer case. The wear plate may be comprised of alumina, steel, or other material(s). The transducer case will typically be metal and grounded to protect electrical connections from electromagnetic interference. In some embodiments, the shear ring element will be packaged in a damping material to increase the transducer's resonant bandwidth. The sensing element and electrical connections are typically entirely potted in an epoxy or other material to protect them from environmental degradation.

Various means of guided wave transduction exist, including piezoelectric transducers, electromagnetic acoustic transducers (EMATs), impact devices, and magnetostrictive transducers. Any of these transduction types, operating in shear horizontal mode, can be used as AE sensors to detect $SH_0$ mode AE events. Beyond the use of circumferentially-poled piezoceramic transducers, magnetostrictive transducers will be used as another example sensor that will be useful for AE. Magnetostrictive transducers have been utilized for the purposes of ultrasonic guided wave generation and reception since the 1970s, and have more recently been utilized for the purposes of long-range pipe inspection in axisymmetric and segmented configurations. However, it appears that little, if any, work has been done to explore their use as AE sensors. A magnetostrictive ("MS") sensor can also be used as an AE receiver.

Figure 10:
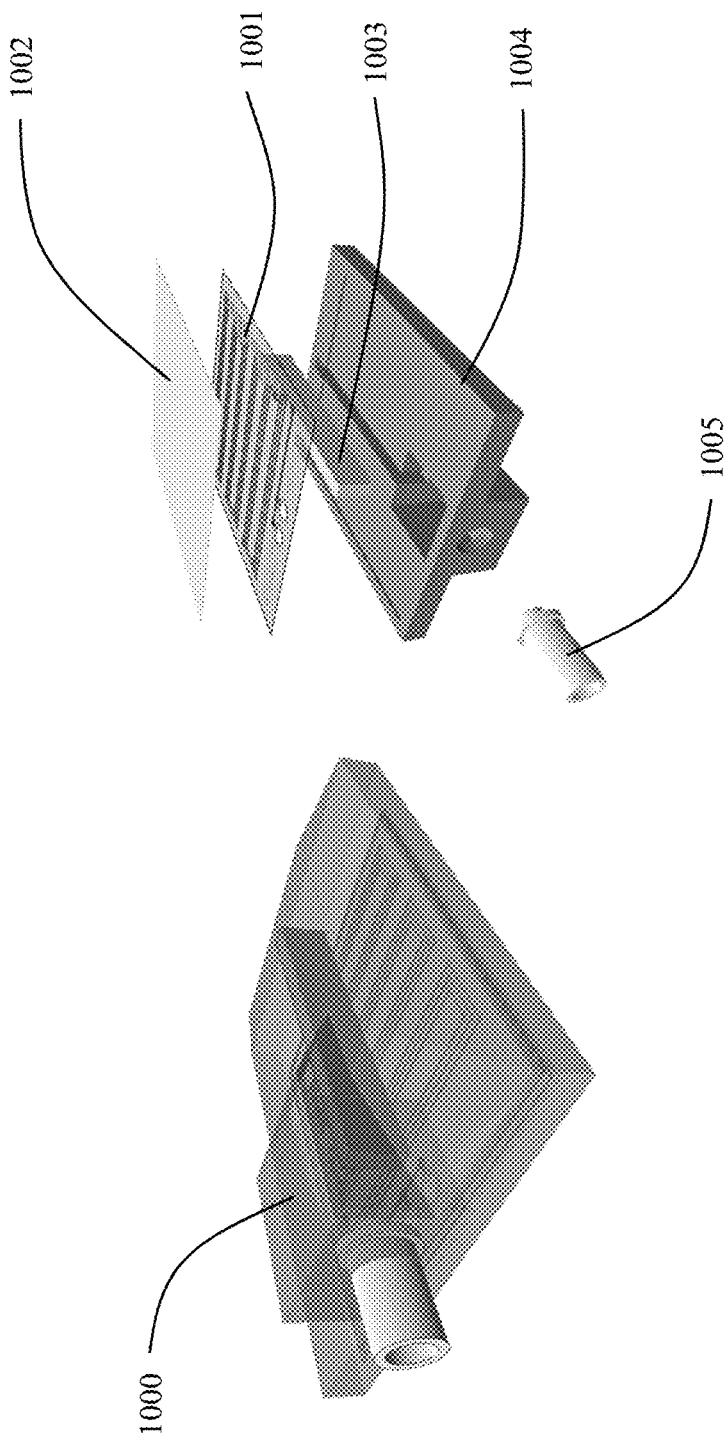
FIG. 10 illustrates the components of a magnetostrictive sensor in accordance with some embodiments.

FIG. 10 illustrates one example of a magnetostrictive sensor 1000 in accordance with some embodiments. Magnetostrictive sensor 1000 includes a sensor coil 1001, MS material 1002, a means to create a biasing magnetic field 1003, sensor housing 1004, and a connector 1005. The sensor coil 101 may be a flat flexible cable ("FFC") or a flexible printed circuit board ("FPCB"), to list only a couple of possibilities. The wiring of the FFC or trace design of the FPCB are configured to control the mode and wavelength of the guided waves that are generated and detected by the coil. MS material 1002 can include iron cobalt (FeCo), due to its high efficiency, or other suitable materials as will be understood by one of ordinary skill in the art. The means for creating a biasing magnetic field 1003 can include, but are not limited to, permanent magnets, electromagnets, combinations thereof, or other devices capable of generating a magnetic field.

A time-varying current in the sensor coil 1001 in the presence of a biasing magnetic field provided by the magnet 1003 generates a time-varying strain (and thus displacement) in the MS material 1002 along the direction of the biasing magnetic field. Conversely, a time-varying displacement in the MS material 1002 results in a time-varying current in the coil 1001. The MS material 1002 is coupled to a surface of the structure to facilitate the sending and/or receiving of waves in the structure.

Figure 11A:
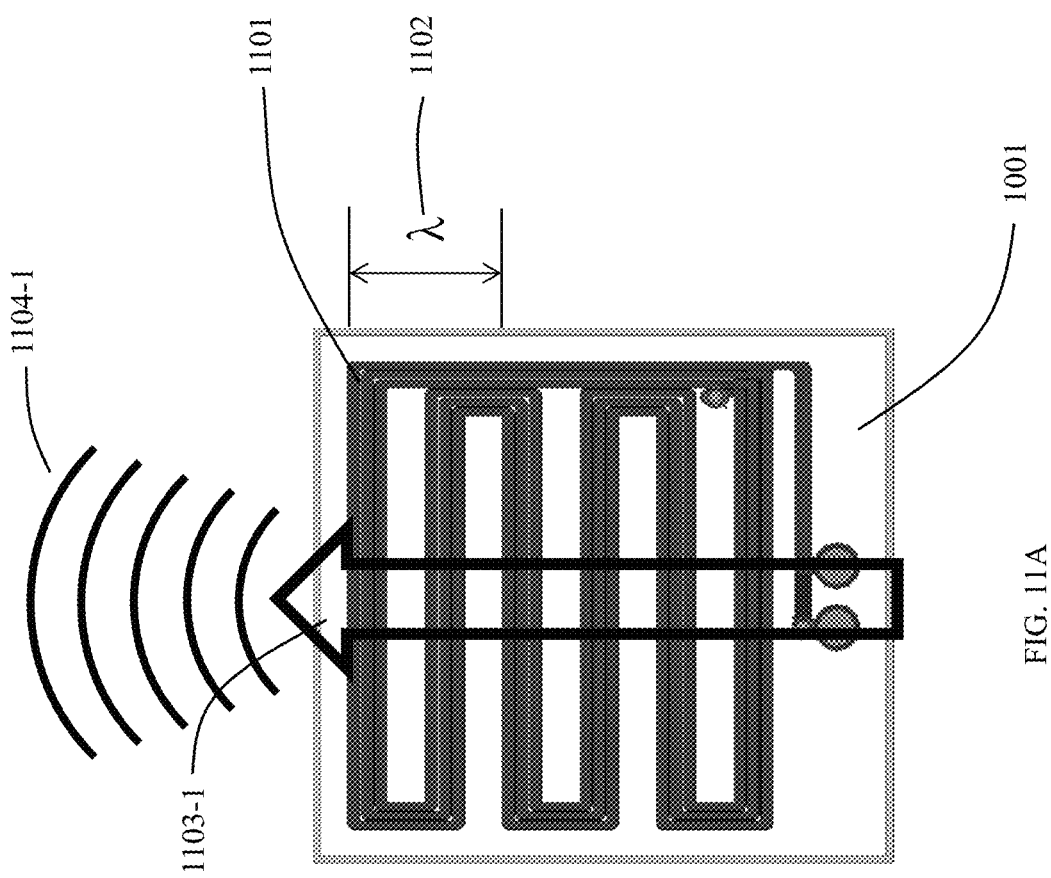
FIG. 11A illustrates a magnetostrictive sensing coil with the biasing magnetic field oriented to produce Lamb-type guided waves in accordance with some embodiments.

FIG. 11A illustrates a magnetostrictive sensing coil 1001 with coil trace 1101 and coil spacing 1102. As noted above and as will be understood a person of ordinary skill in the art, the coil spacing 1102 of coil trace 1101 determines the wavelength, k, of ultrasonic guided waves generated and received by sensing coil 1001. When a biasing magnetic field is applied in the vertical direction, as shown by the arrow 1103-1, Lamb-type guided waves 1104-1 are generated in the vertical direction.

Figure 11B:
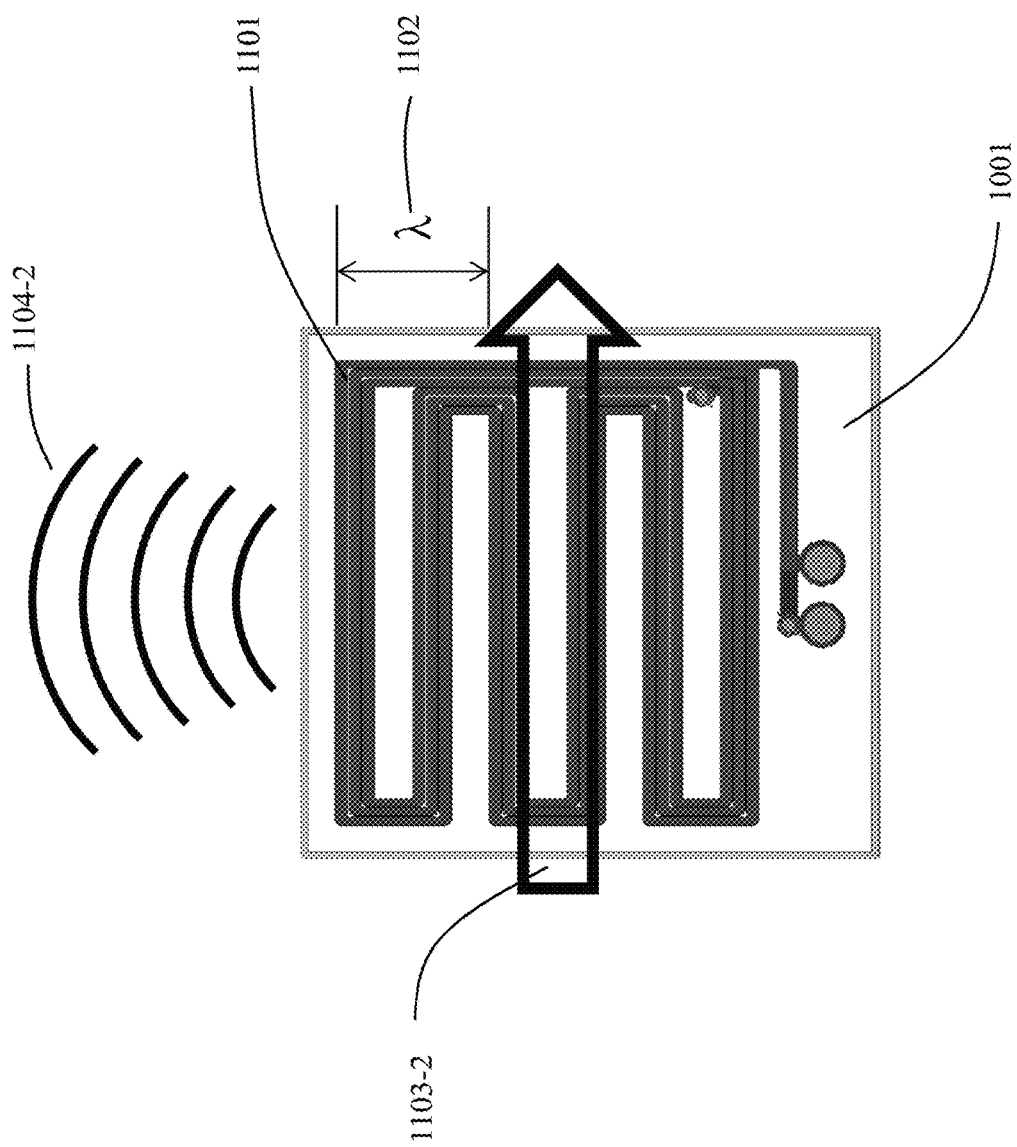
FIG. 11B illustrates a magnetostrictive sensing coil with the biasing magnetic field oriented to produce shear horizontal-type guided waves.

FIG. 11B illustrates the same magnetostrictive sensing coil 1001 depicted in FIG. 11A, but now with a biasing magnetic field in the horizontal direction, as shown by the arrow 1103-2. This configuration generates shear horizontal type guided waves 1104-2 in the vertical direction. Note that the biasing magnetic field arrow may indicate a field that is south-to-north or north-to-south in orientation.

As will be appreciated from the foregoing description of FIGS. 11A and 11B, MS transducers can excite Lamb-type or shear-type guided waves, depending on magnet orientation. An individual coil is designed to operate at a specific wavelength, and therefore can operate over a wide frequency bandwidth, depending on the structure to which it is applied. Due to these properties, MS sensors can be designed to have a high degree of mode control for either receiving or transmitting ultrasonic GWs. Also, the sensors have a high signal-to-noise ratio and can act as an efficient sender of GWs with a relatively low applied voltage (e.g., ±10 V). This is in contrast with piezoelectric ceramics, which typically operate at voltage levels between 100 and 400 V. Additionally, depending on the coil design, these transducers can be highly directional, which can be useful when sending energy along a structure which is predominately 1-dimensional, such as a beam or bar. Furthermore, MS transducers can be implemented to have a lower-profile and be lighter than their piezoceramic counterparts.

Noise due to environmental conditions is an issue in AE testing. When environmental noise is present, the system registers many events due to the noise source, such as rain or wind-driven particles of sand or dirt. The impact of each rain droplet or wind-driven particle on the surface of the monitored structure generates ultrasonic stress waves, and the AE system will register many of those impacts as an AE event. This causes two major problems. First, in even light to moderate rain, the system may be inundated with events, causing the system to be overwhelmed while it attempts to record all of the environmental noise events. In this case, the system is no longer continuously monitoring the structure, and potential real damage events are not recorded. Second, the system has registered a plethora of events, and it may be challenging or even impossible to pick out which events are due to damage as opposed to environmental noise. This increases the complexity of data analysis and can cause errors.

Shear-sensitive AE sensors, by design, will have at least partial immunity to these noise events, causing many fewer events to be registered and allowing continuous data monitoring to occur. Sensors sensitive to the $SH_0$ mode will not register the vast majority of these noise events because they are not good exciters of energy in the $SH_0$ mode. These environmental noise events primarily strike the surface of the structure with an out-of-plane motion that excites the $A_0$ mode. This causes events to be registered by conventional AE sensors because they are highly sensitive to the $A_0$ mode. However, this motion is perpendicular to the $SH_0$ motion, which is why the shear-sensitive sensors are less sensitive to these noise events. Tests during a heavy rain storm have shown very few rain droplet events picked up by shear ring AE sensors. The same will be true for particles blown into or dropped on a structure's surface.

Figure 12:
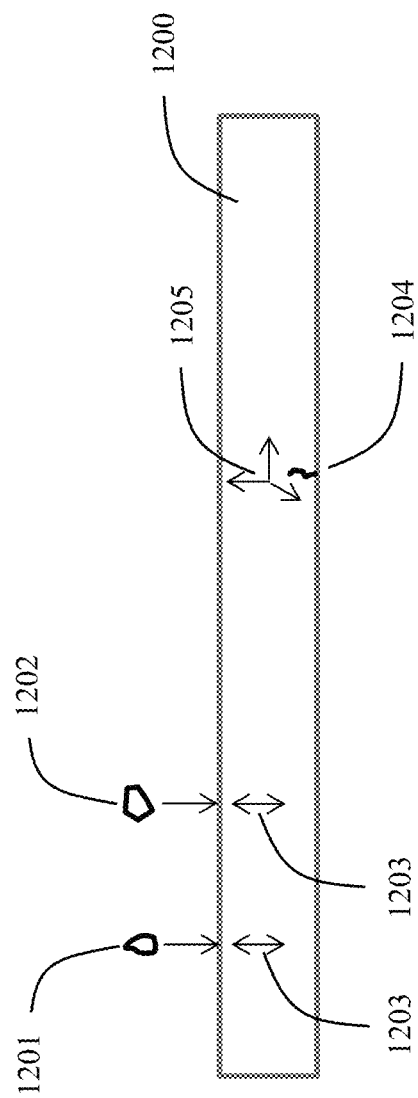
FIG. 12 illustrates rain and wind-driven particles exciting out-of-plane motion in a plate in accordance with some embodiments.

FIG. 12 illustrates several AE noise sources in a plate-like structure 1200. Rain 1201 or wind-driven particulate 1202 impacting the outer surface of a plate primarily generates out-of-plane motion 1203 in the structure 1200. In contrast, an AE damage event such as crack propagation 1204 can generate motion 1205 in all directions which can generate ultrasonic energy in all guided wave modes.

Although there is great benefit to the shear-type AE sensor in terms of environmental noise reduction, there is, advantageously, little loss in terms of sensitivity to real damage events. This is because many damage events produce energy in each of the fundamental GW mode types and therefore are detectable by both conventional and shear-type sensors. An additional advantage of shear-type AE sensors is that they are unaffected by liquid in contact with the structure, such as rain, condensation, or fluid in a tank or pipe. Conventional AE sensors rely on Lamb wave modes, which can be attenuated, distorted, and otherwise negatively affected by surface liquid.

Conventional, commercially-available AE systems utilize a user-defined wave velocity value for AE event localization algorithms. This value is determined in velocity calibration tests conducted by the NDE inspector. Typically, pencil lead breaks ("PLBs") will be performed on the surface of the structure at a sensor location and the time of flight for the event to be registered at an adjacent sensor is recorded. The known distance between the two sensors is divided by the time of flight to estimate the ultrasonic wave velocity in the structure. This test is often performed several times and/or at several sensors to gain confidence in the velocity value. If different results are obtained at different locations of the structure, which can be common, an average, the smallest, or the largest velocity value may be input by the inspector into the AE system software. Incorrect velocity values, or physical velocities which are different on different parts of a structure or at different frequencies, will cause errors in the localization algorithm and AE events will not be located accurately. There are multiple possible sources of error associated with this technique and all of them can be removed by using shear-type AE sensors sensitive to the $SH_0$ GW mode. This is because the $SH_0$ mode has a single wave velocity that is independent of structure thickness and frequency and only depends on the bulk shear wave velocity in the material of which the structure is composed.

Figure 13:
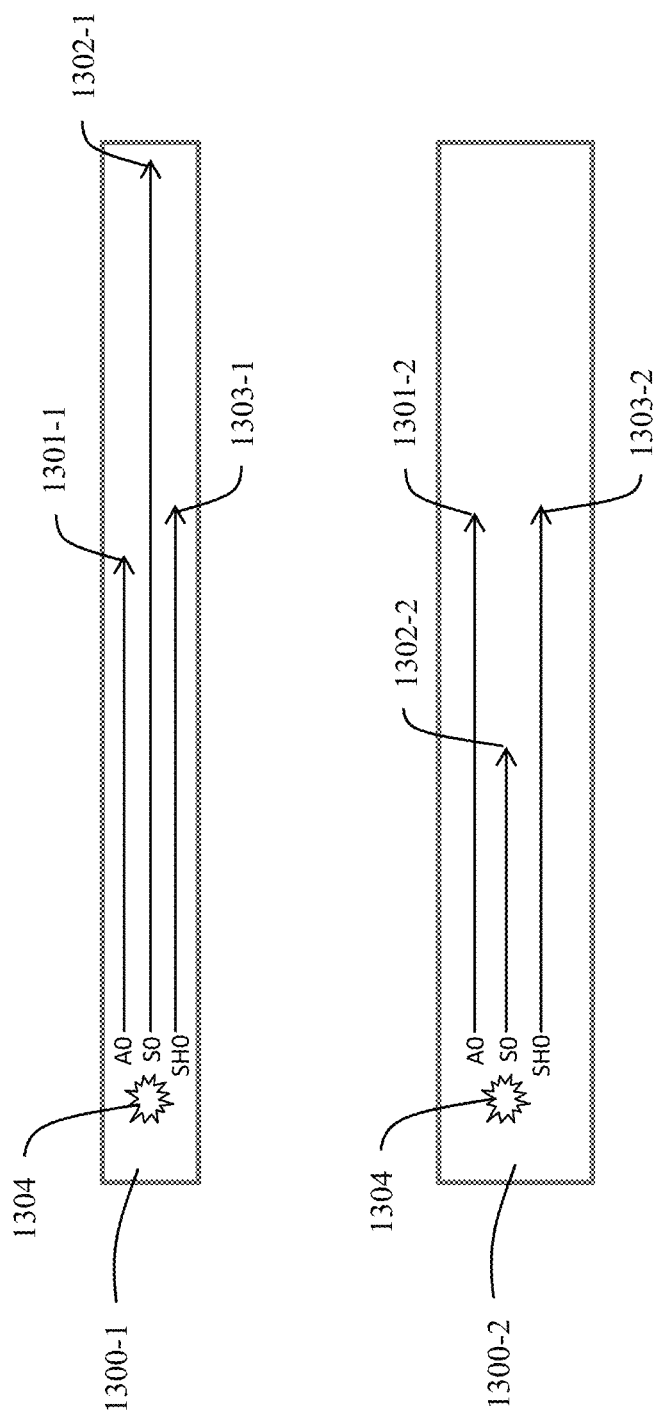
FIG. 13 illustrates different propagation distances for the three fundamental guided wave mode types in two steel plates having different thicknesses in accordance with some embodiments.

FIG. 13 illustrates the concept of different wave velocities in a 0.063"-thick steel plate 1300-1 and a 0.33"-thick steel plate 1300-2 generated from an AE event 1304. At a frequency of 300 kHz, the three fundamental wave modes have different velocities which result in different propagation distances over the same period of time. In the thinner plate 1300-1, the $A_0$ mode has a velocity of 2.93 mm/µs resulting in a propagation distance 1301-1 after time t, the $S_0$ mode has a velocity of 5.35 mm/µs resulting in a propagation distance 1302-1 after time t, and the $SH_0$ mode has a velocity of 3.23 mm/µs resulting in a propagation distance 1303 after time t. In the thicker plate 1300-2, at the same frequency, the $A_0$ mode has a velocity of 3.19 mm/µs resulting in a propagation distance 1301-2 after time t, the $S_0$ mode has a velocity of 1.75 mm/µs resulting in a propagation distance 1302-2 after time t, and the $SH_0$ mode has a velocity of 3.23 mm/µs resulting in the same propagation distance 1303 as in plate 1300—after time t. Here the first Lamb-type wave arrival switches between the $S_0$ and $A_0$ modes and has different velocities in these two cases. However, the $SH_0$ wave arrival is the same in both plates.

Errors in the user-performed velocity calibration using conventional AE sensors arise for a variety of reasons. First, the trigger level may be set at such a value to trigger off of the $A_0$ mode in some cases and the $S_0$ mode in others. These modes typically have significantly different velocities in a structure. At low frequency, the $S_0$ mode is faster and the $A_0$ mode is slower, however, the $A_0$ mode is usually detected with much higher amplitude due to source-matching with surface PLBs. The distance that the wave travels will affect the wave amplitude received by the sensor, which may be too low to exceed the trigger level at longer sensor distances. This is because the wave amplitude decreases as the distance the wave has travelled increases. Second, both the attenuation and dispersion of each mode will affect the relative amplitudes of the modes at different sensor distances. This could also affect which mode sets off the trigger, causing large errors in the apparent wave velocity. Third, for thicker plates or higher-frequency sensing, additional higher-order GW modes may be present (i.e., $S_1, S_2, \ldots, A_1, A_2, \ldots, SH_1, SH_2, \ldots$) which also have different velocities at different frequencies and for different plate thicknesses. This is particularly problematic if the AE source generates more energy into a mode which is different than the modes generated during the PLB calibration test.

These errors will not occur when using shear-type AE sensors and the $SH_0$ mode. Since the velocity of the guided wave is the same for a given material, regardless of thickness or frequency, the velocity can be set automatically in the AE analysis software based on the known bulk shear wave velocity of the material of the structure. Note that the velocity of the $SH_0$ mode is the same as that for bulk shear waves in the material. This removes the source of error by the user inputting an incorrect velocity in the software, as well as velocity calibration tests resulting in the incorrect or an inappropriate velocity. The threshold level is set to trigger off of a single mode—the $SH_0$ mode—and errors due to different relative mode amplitudes become much less of a concern, since the shear-type sensor is generally insensitive to the other modes ($A_0$ and $S_0$), so the $SH_0$ mode is generally the only detectable mode.

When locating in one dimension on a bar, rail, beam, or other similar structure, two (or more) sensors can locate an event between them based on the difference in arrival time at the two sensors for the same event. When locating in two dimensions on a plate, shell, hull, or other similar structure, three (or more) sensors can locate an event inside the sensor array. When locating on a more complex structure, an array of sensors can be placed over areas of different thickness, shape, and connecting regions, and the AE source location may still be determined accurately. Use of the $SH_0$ mode for locating AE damage events can provide an added benefit because the sensor array can cover complex and connecting areas, which may not be covered in the same array in conventional AE testing.

The result of using the $SH_0$ mode for localization is that overall the localization algorithm is more robust and consistent. This consistency will apply across different structures with different shapes and thicknesses. It also applies to AE testing at different frequencies, which may be necessary due to noise sources such as vibrations from nearby equipment or other noise sources that are present in some scenarios. Better localization of AE damage events leads to an earlier reliable detection of damage and can therefore lead to earlier assessment, maintenance planning, and repair.

AE is an excellent inspection method for the detection of impacts, active cracking, active corrosion, and other damage mechanisms. The use of AE sensors in passive mode, i.e., not actively transmitting wave energy into the structure using a transducer, is effective at noting damage initiation and crack and corrosion growth. Typical AE inspection setups involve an array of sensors around an area of known interest where damage may occur. AE events registered by the AE system are processed through a velocity-based triangulation algorithm to assign a location. When many events occur at/near the same location, it is assumed that damage growth is occurring there. All of this is done in a passive mode.

However, AE technology is not as effective at measuring damage severity because defects are not directly sized. AE data can give an estimate of defect size based on the number of events that have occurred, but cannot provide information how large or severe a particular damage site is. Also, if environmental noise causes downtime in data collection, the damage estimate can be artificially low.

GW is an active inspection method in which ultrasound is introduced to a structure to interrogate it for defects. The transmitted GW signals interact with the structure and any defects, and is then received either by the same transmitting sensor (pulse-echo mode) or by a separate receiving sensor (through-transmission mode). Signal characteristics give an indication of damage presence. Very small amounts of damage can be detected when comparing signals to a baseline case. Damage, such as a crack in a beam, can be directly sized based off of the signal by extracting characteristics such as the reflected wave amplitude or energy. The guided wave mode and frequency selected can be used to optimize detection and sizing of different damage types.

The combination of these two inspection methods (AE and GW) can provide increased reliability and detection capabilities over either method individually. Passive AE sensing can be used to detect damage events and monitor damage progression. AE events can act as a trigger for the inspection system to perform active GW sensing, and GW sensing can actively size the defect.

The $SH_0$ GW mode is particularly useful in active GW sensing because its displacement profile is constant through the thickness of a plate. This means that a crack with a given depth will have a reflection amplitude proportional to the crack's depth (or length). This is often not true for $A_0$ and $S_0$ Lamb-type GWs, for which the energy is not evenly distributed through the structure's thickness but is typically concentrated toward the surface, plate center, or other area.

The combination of passive AE and active GW sensing into a single probe is possible and desirable. One option is to use a shear-sensitive sensor that can perform both inspection types. Examples of this sensor are a shear ring piezoelectric sensor or a shear-type magnetostrictive sensor. These sensors can act as both passive AE receivers, or as active GW sender/receivers.

Another option is to include different sensing elements in probes adjacent to each other, or to package two (or more) different sensing elements within the same probe. There are a variety of designs that would make this possible.

Figure 14A:
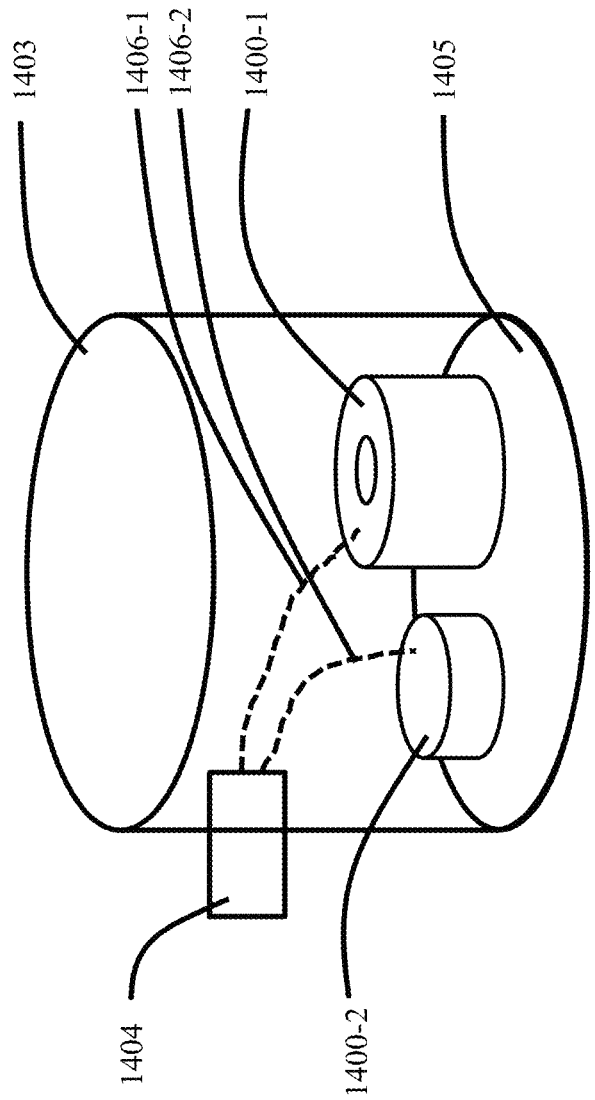
FIG. 14A illustrates one example of a probe configuration with one shear ring element and one disk element within the same probe housing in accordance with some embodiments.
Figure 14B:
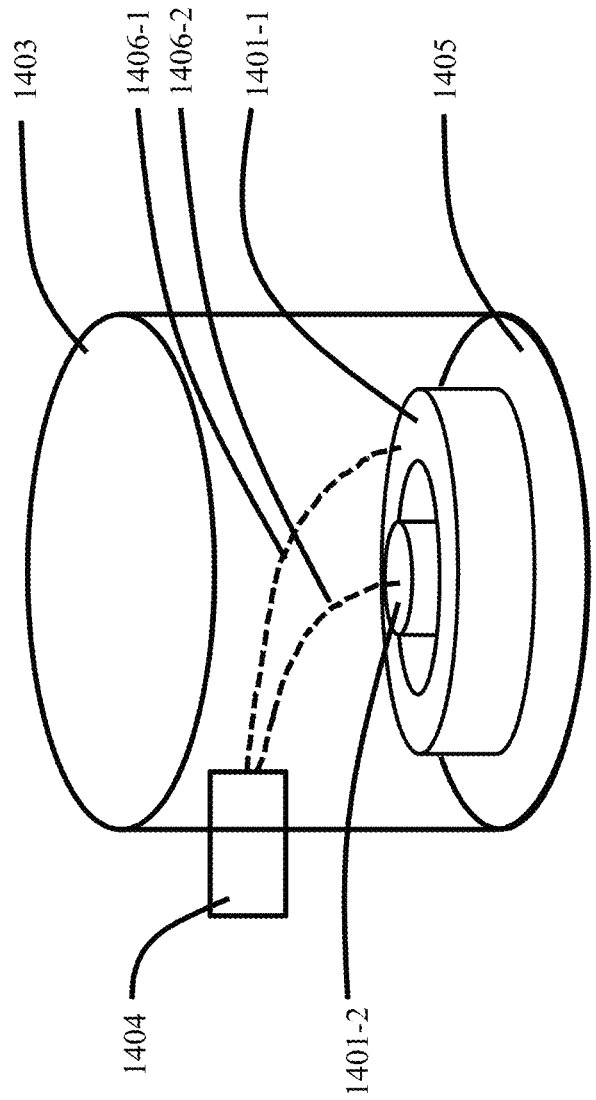
FIG. 14B illustrates another example of a probe configuration with one shear ring element and one disk element within the same probe housing in accordance with some embodiments.
Figure 14C:
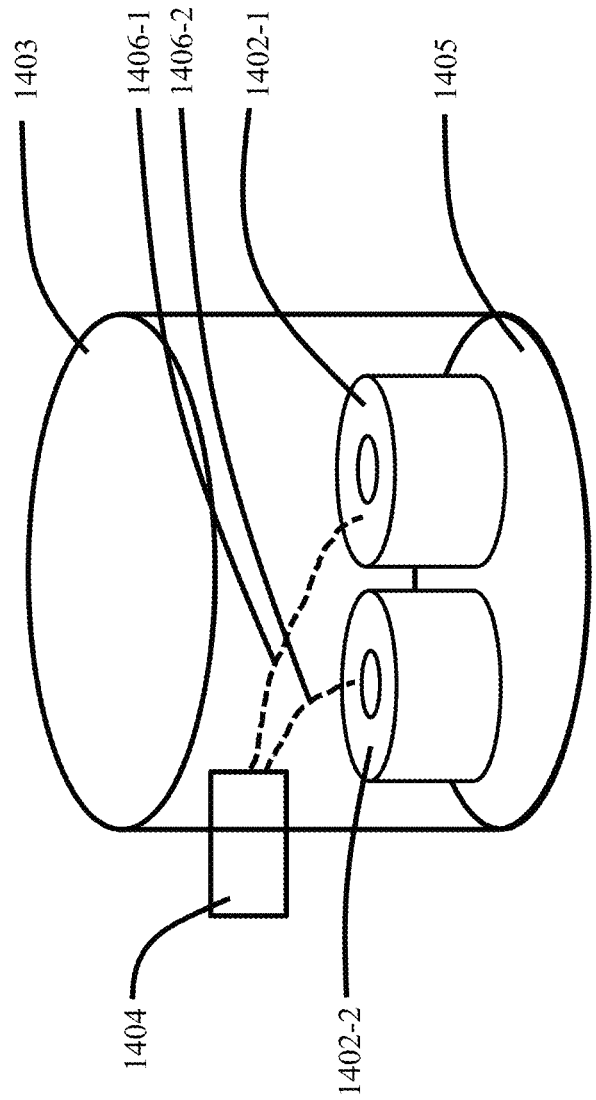
FIG. 14C illustrates one example of a probe configuration with two shear ring elements within the same probe housing in accordance with some embodiments.

FIGS. 14A, 14B, and 14C illustrate several possible probe designs where multiple sensing elements are packaged within the same probe housing 1403. In FIG. 14A, a shear ring element 1400-1 is configured next to an piezoelectric disk element 1400-2. In FIG. 14B, an piezoelectric disk element 1401-2 having an outer diameter that is smaller than the inner diameter of the shear ring element 1401-1 so that the piezoelectric disk 1401-2 is configured within the shear ring element 1401-1. Design 1403, in FIG. 14C, illustrates two shear ring elements 1402-1 and 1402-2 are configured next to each other. The two shear ring elements 1402-1 and 1402-2 could also be configured concentrically.

In each probe embodiment illustrated in FIGS. 14A, 14B, and 14C, the bottom of the two elements are configured on approximately the same plane within the probe housing such that they can be simultaneously coupled to the surface of a structure. The housing 1403 may further comprise a connector 1404 and face plate 1405. Wires 1406-1 and 1406-2 create the electrical connection between the connector and the piezoelectric elements and are coupled to a controller (not shown), such as controller 1730 shown in FIG. 17. The elements in FIGS. 14A, 14B, and 14C may each be passive or active elements. Furthermore, each of these probe configurations illustrated in FIGS. 14A, 14B, and 14C may be packaged with a damping material to increase the bandwidth of the transducer's resonance.

Examination of the shear horizontal mode and Lamb-mode signals can be used to characterize a source of an acoustic emission. Relative amplitude and other features of the mode content can help identify the damage type that was the source of the emission (e.g., crack damage, corrosion damage, etc.). Analysis of features such as frequency content, duration, counts, maximum amplitude, and other acoustic emission features can be used in conjunction with mode type information to further characterize a source of acoustic emissions. Additionally, similar characterization techniques can be applied to differentiate between a damage event, e.g. crack growth or active corrosion, or a non-damage event, e.g. rain, wind-blown debris, or intermittent contact, as the source of the acoustic emission.

In conventional AE instrumentation of a complex structure, dissimilar sections of a structure will be instrumented with distinct sensor arrays. This is because each section of a structure may have different wave propagation characteristics for $A_0$ and $S_0$ modes, due to a difference in thickness, for example, which leads to a different GW mode velocity. Errors in velocity-based triangulation will occur if each area is not analyzed separately. However, when using the $SH_0$ mode, the GW velocity is not dependent on the structure thickness or frequency. For this reason, a single array of sensors can be used for damage localization algorithms.

Examples of complex structures include a tower with support beams, support posts, and platforms of different thicknesses, a coupler in a pipeline, and a ship hull where two plates of different thicknesses are welded together. All of these structures contain areas with different thicknesses, and thus different guided wave mode velocities and the need for separate conventional AE sensor arrays to accurately localize defects.

However, when using the $SH_0$ mode, the wave velocity is independent of the structure's thickness. This allows for the use of one array, all with the same wave velocity for the localization algorithm. This is an important advantage as, in many structures, damage can often occur at the junction between two dissimilar sections. The following figure illustrates this point for two plates of similar material but different thicknesses welded together, where cracking may occur at the weld joining the two sections.

Figure 15A:
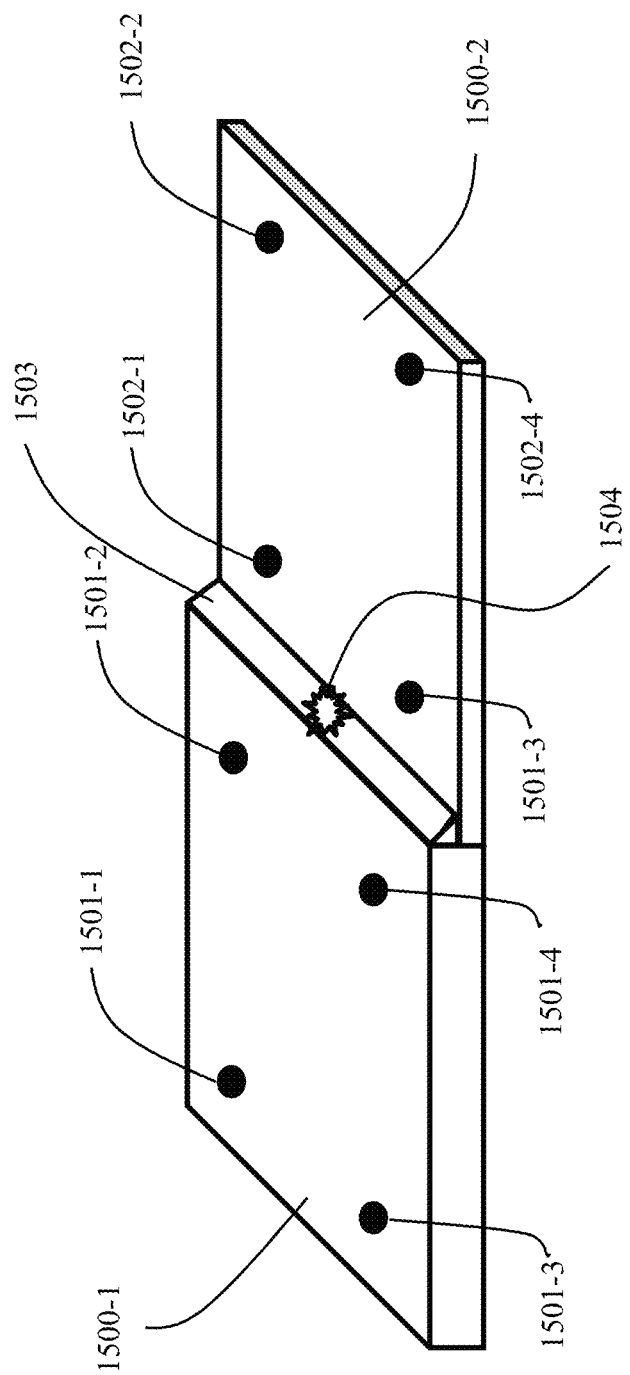
FIG. 15A illustrates two conventional AE sensor arrays on a structure composed of two welded plates having different thicknesses in accordance with some embodiments.

FIG. 15A illustrates a thicker plate 1500-1 attached to a thinner plate 1500-2 by a welded section 1503. Because Lamb-type mode velocities at the same frequency are different in the two plates, one sensor array 1501, comprised of conventional AE sensors 1501-1 through 1501-4, is applied to the thicker plate 1500-1 and a second sensor array 1502, comprised of conventional AE sensors 1502-1. 1502-2, . . . 1502-4, is applied to the thinner plate 1500-2. Two sensor arrays are used because there are two arrays used for damage localization due to the different velocities. An AE event 1504 due to damage will not be correctly located due to the disparate velocities causing errors in the velocity-based localization algorithm. This issue is not present for arrays which locate using the $SH_0$ mode.

Figure 15B:
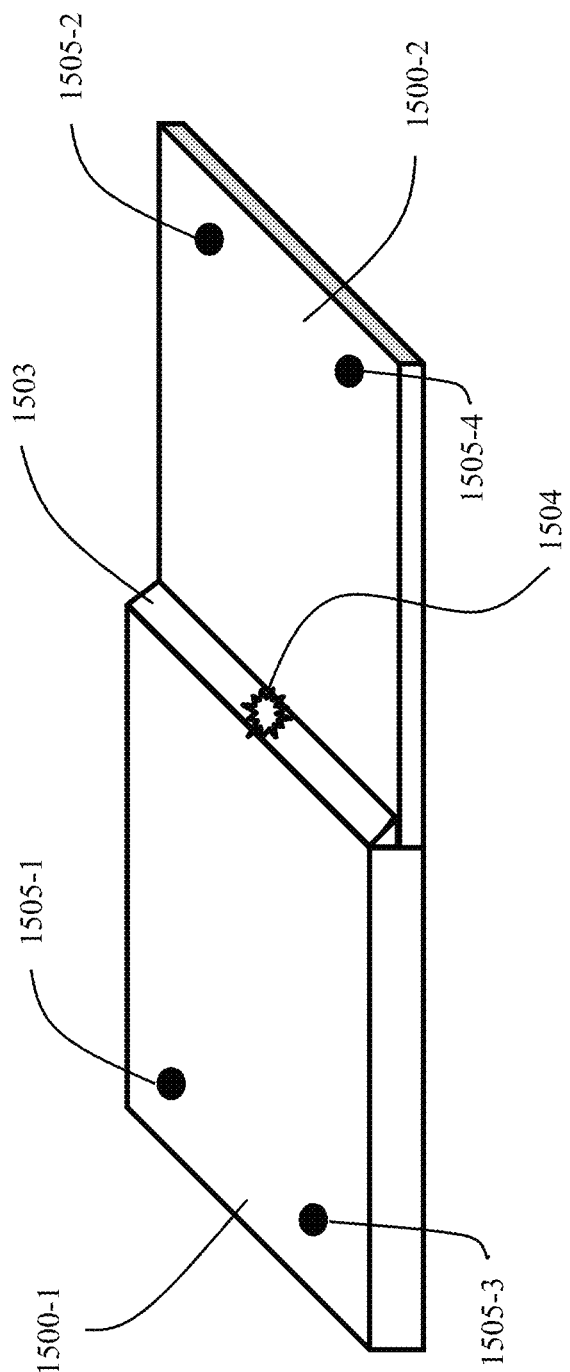
FIG. 15B illustrates a single shear-type AE sensor array on a structure composed of two welded plates having different thicknesses in accordance with some embodiments.

FIG. 15B illustrates the same welded plates 1500-1, 1500-2 now with a single sensor array 1505, comprised of shear-type AE sensors 1505-1, 1505-2, . . . , 1505-4. In this case, the velocity of the guided wave mode is equal in the two plate sections, because the $SH_0$ mode velocity is not dependent on structure thickness or frequency, only on material type. An AE event 1504 due to damage will be correctly identified and localized by the sensor array 1505, due to the use of shear-type sensors. Additionally, fewer sensors can be used to monitor damage in the same area compared to what is required for conventional AE.

Active guided wave computed tomography ("CT"), such as those described in Rose, J. L., Ultrasonic Guided Waves in Solid Media, Cambridge University Press, New York, N.Y., 2014, can be performed to create a damage map of the area and assess damage severity. The same sensor array can be used for the active CT scan as for the passive AE scan. A CT damage map is created by analyzing the signals sent between pairs of sensors in the current damage state to a previous damage state or baseline state. These damage maps have the potential to inform the inspector regarding the damage location, extent, and most importantly the current severity of the damage, which conventional AE systems can be unable to do. Data from passive AE sensing could also be used to refine the damage location on the damage map or provide a starting point for data analysis. The CT data is typically adjusted for environmental factors such as temperature that changes signals but is not correlated with damage. A variety of signal features may be used to create the CT damage map, including but not limited to: amplitude, amplitude ratio, wave packet arrival time, frequency at max amplitude, frequency shift, frequency ratio, wave packet kurtosis, FFT kurtosis, and skew.

Figure 16A:
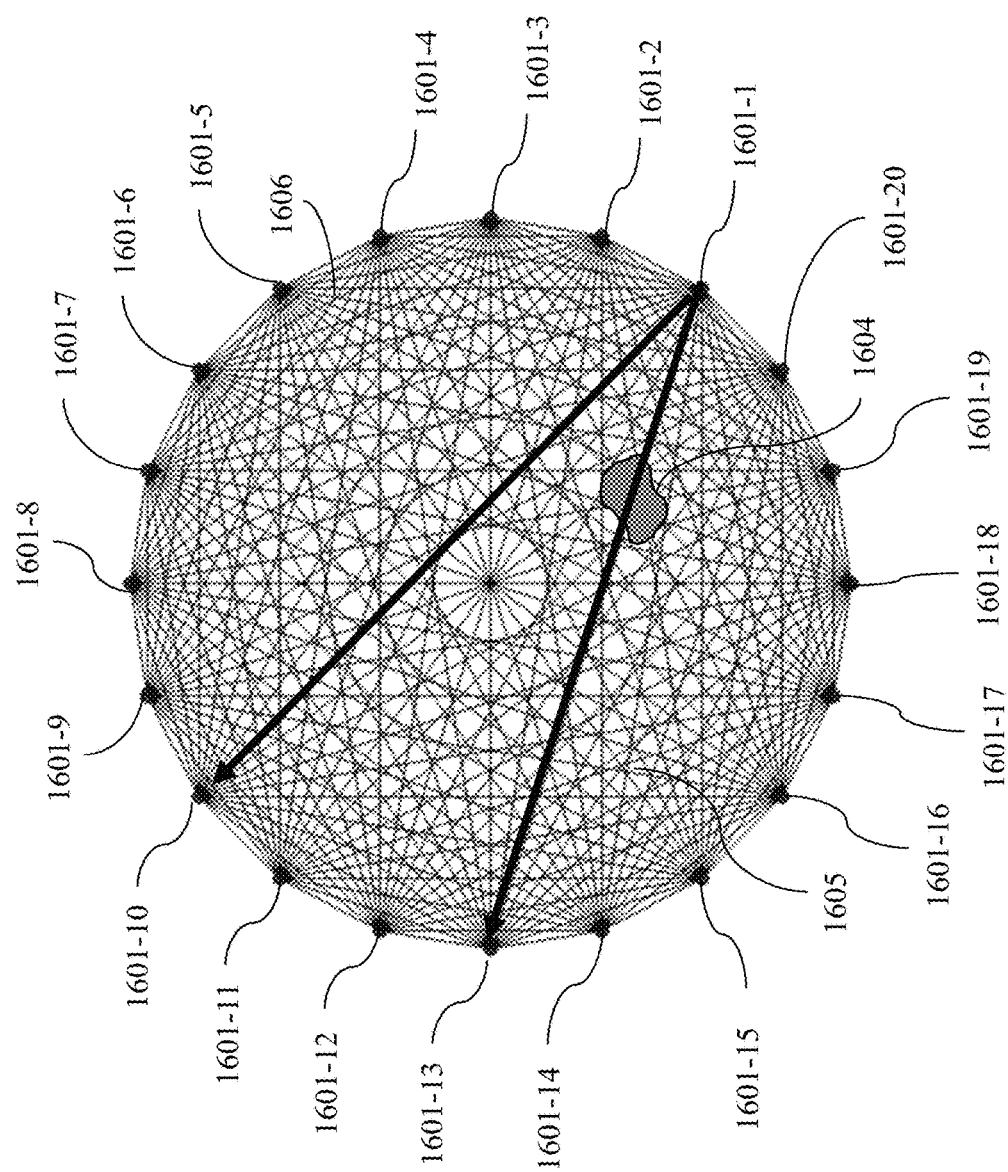
FIG. 16A illustrates an array of shear ring sensors around the perimeter of an area to be monitored with guided wave CT imaging in accordance with some embodiments.
Figure 16B:
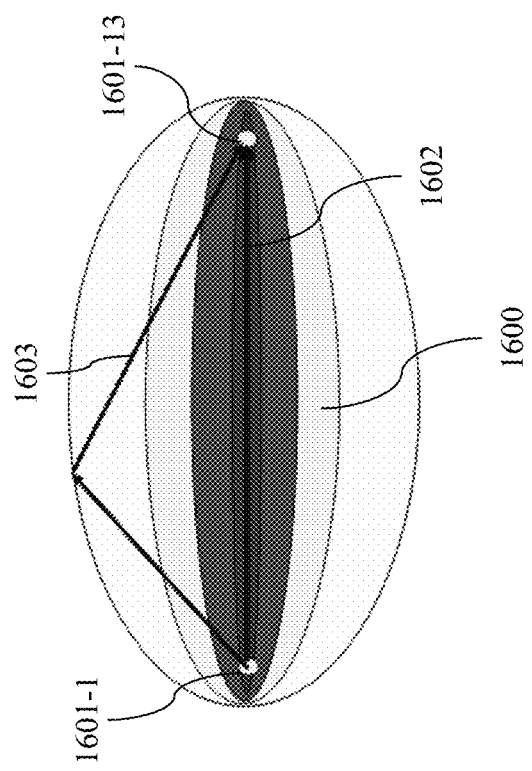
FIG. 16B illustrates a probability density function between two transducer elements of a guided wave CT imaging array in accordance with some embodiments.
Figure 16C:
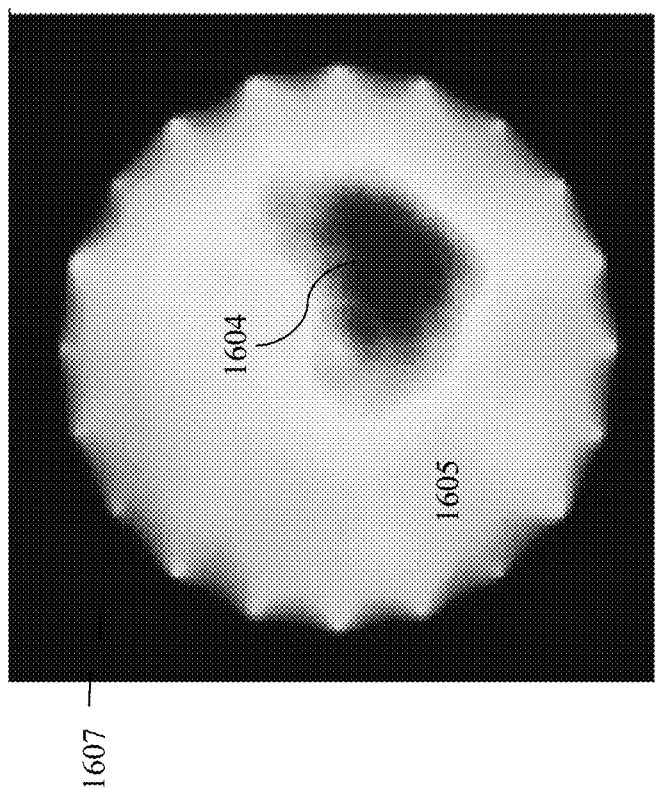
FIG. 16C illustrates one example of a pseudo-image of damage in a plate-like structure generated with a guided wave CT imaging array in accordance with some embodiments.

FIGS. 16A, 16B, and 16C illustrate one embodiment in which at least two shear ring elements 1601 (i.e., 1601-1, 1601-2, . . . 1601-20) are coupled to a structure around the perimeter of an area 1605 to be monitored using guided wave CT imaging. Although 20 shear ring elements 1601 are illustrated in FIG. 16A, one of ordinary skill in the art will understand fewer or more shear ring elements 1601 can be implemented. SH wave signals are transmitted between the elements 1601 in the array. A damage probability function 1600, shown in FIG. 16B, which accounts for both direct 1602 and indirect 1603 wave paths, is mapped onto each signal path 1606 and, as shown in FIG. 16C, scaled according to at least one signal parameters to generate a pseudo-image 1607 of damage 1604 in the structure within the array perimeter. In some examples of this embodiment, baseline data are used as a reference comparison for the guided wave signals.

Figure 17:
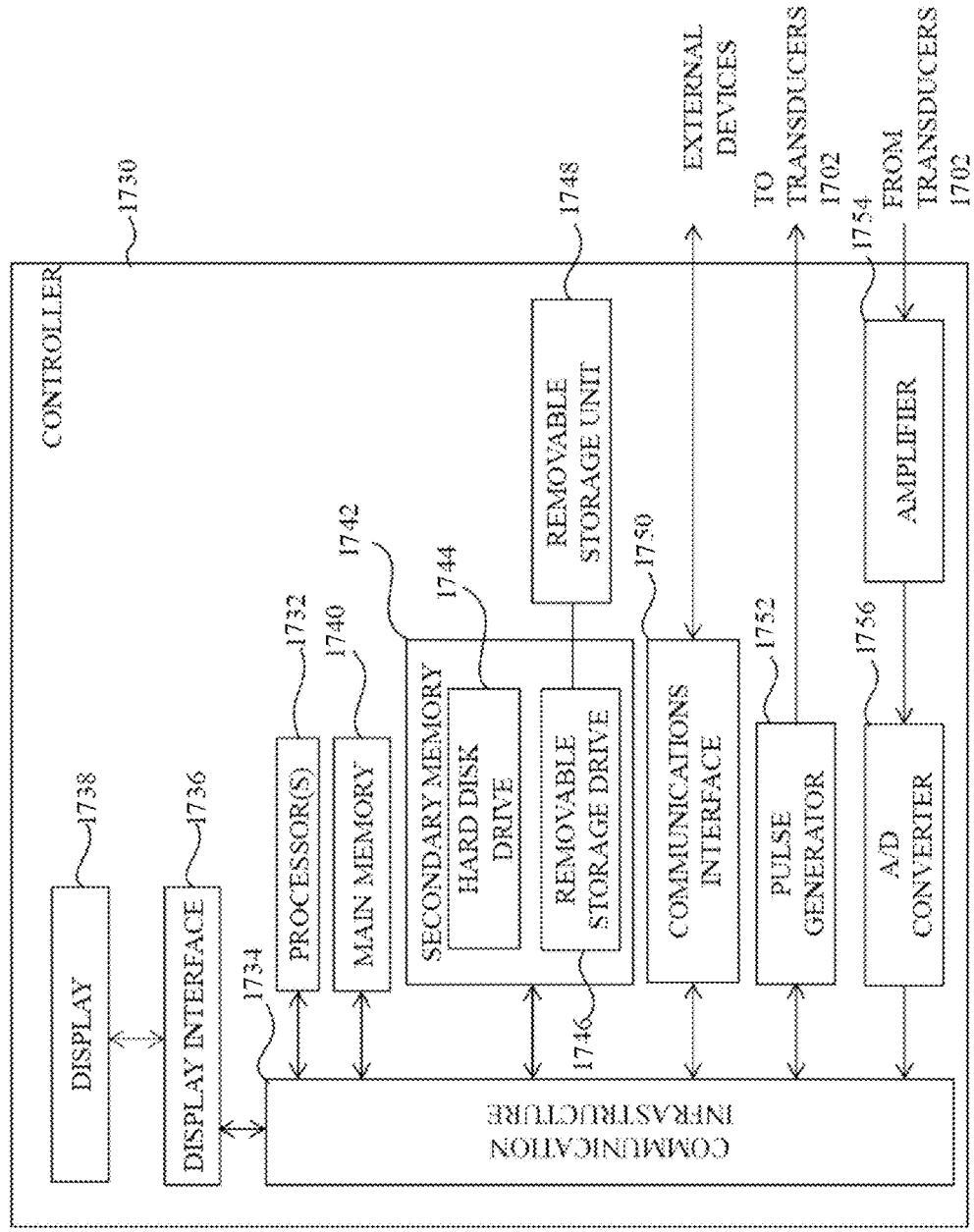
FIG. 17 illustrates one example of a block diagram of a controller of the non-destructive inspection system in accordance with some embodiments

Referring now to FIG. 17, one example of a block diagram of a controller 1730 is shown. The controller 1730 is configured to be coupled to the plurality of transducers 1702. The controller 1730 includes one or more processors, such as processor(s) 1732. Processor(s) 1732 may be any central processing unit ("CPU"), microprocessor, microcontroller, or computational device or circuit for executing instructions and be connected to a communication infrastructure 1734 (e.g., a communications bus, cross-over bar, or network). Various software embodiments are described in terms of this exemplary controller 1730. After reading this description, it will be apparent to one of ordinary skill in the art how to implement the method using other computer systems or architectures.

In some embodiments, controller 1730 includes a display interface 1736 that forwards graphics, text, and other data from the communication infrastructure 1734 (or from a frame buffer not shown) for display on a monitor or display unit 1738 that is integrated with or separate from controller 1730.

Controller 1730 also includes a main memory 1740, such as a random-access memory ("RAM"), and a secondary memory 1742. In some embodiments, secondary memory 1742 includes a persistent memory such as, for example, a hard disk drive 1744 and/or removable storage drive 1746, representing an optical disk drive such as, for example, a DVD drive, a Blu-ray disc drive, or the like. In some embodiments, the removable storage drive may be an interface for reading data from and writing data to a removable storage unit 1748. Removable storage drive 1746 reads from and/or writes to a removable storage unit 1748 in a manner that is understood by one of ordinary skill in the art. Removable storage unit 1748 represents an optical disc, a removable memory chip (such as an erasable programmable read only memory ("EPROM"), Flash memory, or the like), or a programmable read only memory ("PROM")) and associated socket, which may be read by and written to by removable storage drive 1746. As will be understood by one of ordinary skill in the art, the removable storage unit 1748 may include a non-transient machine-readable storage medium having stored therein computer software and/or data.

Controller 1730 may also include one or more communication interface(s) 1750, which allows software and data to be transferred between controller 1730 and external devices such as, for example, transducers 1702 and optionally to a mainframe, a server, or other device. Examples of the one or more communication interface(s) 1750 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, or any combination thereof. Software and data transferred via communications interface 1750 are in the form of signals, which may be electronic, electromagnetic, optical, or other signals capable of being received by communications interface 1750. These signals are provided to communications interface(s) 1750 via a communications path or channel. The channel may be implemented using wire or cable, fiber optics, a telephone line, a cellular link, a radio frequency ("RF") link, or other communication channels.

In this document, the terms "computer program medium" and "non-transient machine readable medium" refer to media such as removable storage units 1748 or a hard disk installed in hard disk drive 1744. These computer program products provide software to controller 1730. Computer programs (also referred to as "computer control logic") may be stored in main memory 1740 and/or secondary memory 1742. Computer programs may also be received via communications interface(s) 1750. Such computer programs, when executed by a processor(s) 1732, enable the controller 1730 to perform the features of the method discussed herein.

In an embodiment where the method is implemented using software, the software may be stored in a computer program product and loaded into controller 1730 using removable storage drive 1746, hard drive 1744, or communications interface(s) 1750. The software, when executed by a processor(s) 1732, causes the processor(s) 1732 to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Controller 1730 also includes a pulse generator 1752 configured to output a variety of pulses to transducers 1702, which can be any of the transducers described herein, including the transducers illustrated in FIGS. 14A-14C. For example, pulse generator 1752 may transmit time-delayed control signals to transducers 1702 and/or pulse generator 1752 may transmit control signals of varying amplitudes to transducers 1702.

An amplifier 1754 is configured to amplify signals received from transducers 1702. Such signals received by transducers 1702 include reflections of waves from structural features and other anomalies, e.g., corrosion in a plate or plate-like structures, in response to signals transmitted by pulse generator 1752. An analog to digital ("A/D") converter 1756 is coupled to an output of amplifier 1754 and is configured to convert analog signals received from amplifier 1754 to digital signals. The digital signals output from A/D converter 1756 may be transmitted along communication infrastructure 1734 where they may undergo further signal processing by processor(s) 1732 as will be understood by one of ordinary skill in the art.

In some embodiments, the disclosed methods can be embodied at least partially in the form of program code embodied in tangible media, such as floppy diskettes, CD-ROMs, DVD-ROMs, Blu-ray disks, hard drives, solid-state drives, Flash memory drives, or any other machine-readable storage medium, wherein, when the program code is loaded into and executed by a machine, such as a computer, the machine becomes an apparatus for practicing the method. The disclosed methods also can be at least partially embodied in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the method. When implemented on a general-purpose processor, the program code segments combine with the processor to provide a unique device that operates analogously to specific logic circuits.

Although the systems and methods have been described in terms of exemplary embodiments, they are not limited thereto. Rather, the appended claims should be construed broadly, to include other variants and embodiments of the disclosed systems and methods, which may be made by those skilled in the art without departing from the scope and range of equivalents of the systems and methods.

The invention claimed is:

1. A system, comprising:
    at least one circumferentially-polarized $d_{15}$ shear ring transducer configured to be disposed on a structure and to detect at least one shear horizontal-type acoustic emission from damage to the structure; and
    a controller electrically coupled to the at least one circumferentially-polarized $d_{15}$ shear ring transducer, the controller including
        a machine-readable storage medium, and
        a processor in signal communication with the machine-readable storage medium, wherein the processor is configured to store acoustic emission signal data in the machine-readable storage medium when a signal amplitude detected by the at least one circumferentially-polarized $d_{15}$ shear ring transducer crosses a first threshold.

2. The system of claim 1, wherein
    the at least one circumferentially-polarized $d_{15}$ shear ring transducer includes a plurality of circumferentially-polarized $d_{15}$ shear ring transducers, and
    the processor is configured to calculate a location of a source of the at least one shear horizontal-type acoustic emission in said structure using a source location algorithm using a shear wave velocity in said structure and the acoustic emission signal data.

3. The system of claim 1, wherein
the structure is a plate,
the at least one circumferentially-polarized $d_{15}$ shear ring transducer includes a plurality of circumferentially-polarized $d_{15}$ shear ring transducers, and
the processor is configured to identify a location of a source of the at least one shear horizontal-type acoustic emission in said plate using a synthetic focusing back-propagation algorithm.

4. The system of claim 1, wherein the at least one circumferentially-polarized $d_{15}$ shear ring transducer is configured to
detect shear horizontal-type acoustic emissions within at least one first frequency band, and
detect Lamb-type acoustic emissions within at least one second frequency band; and
wherein the processor is configured to store shear horizontal-type and Lamb-type acoustic emission signal data in the machine-readable storage medium when the signal amplitude detected by the at least one circumferentially-polarized $d_{15}$ shear ring transducer crosses at least one of a first threshold in the at least one first frequency band or a second threshold in the at least one second frequency band.

5. The system of claim 4, wherein
the at least one circumferentially-polarized $d_{15}$ shear ring transducer includes a plurality of circumferentially-polarized $d_{15}$ shear ring transducers; and
the processor is configured to calculate a location of a source of the at least one shear horizontal-type acoustic emissions in said structure using a source location algorithm, at least one guided wave velocity in the structure, and the shear horizontal-type and Lamb-type acoustic emission signal data.

6. The system of claim 4, wherein the processor is configured to characterize a source of the shear horizontal-type acoustic emissions based on relative characteristics of the shear horizontal-type acoustic emissions in the at least one first frequency band and the Lamb-type acoustic emissions in the at least one second frequency band detected by the at least one circumferentially-polarized $d_{15}$ shear ring transducer.

7. The system of claim 1, wherein the at least one circumferentially-polarized $d_{15}$ shear ring transducer includes at least one multi-element transducer, the at least one multi-element transducer comprising:
at least one circumferentially-polarized $d_{15}$ shear ring element configured to detect shear horizontal-type acoustic emissions, and
at least one disk-shaped $d_{33}/d_{13}$-type piezoelectric element configured to detect Lamb-type acoustic emissions; and
wherein the processor is configured to store shear horizontal-type and Lamb-type acoustic emission signal data in the machine-readable storage medium when at least one of an amplitude of the shear horizontal-type acoustic emissions detected by the at least one circumferentially-polarized $d_{15}$ shear ring element crosses a first threshold or an amplitude of the Lamb-type acoustic emissions detected by the at least one disk-shaped $d_{33}/d_{13}$-type piezoelectric element crosses a second threshold.

8. The system of claim 7, wherein
the at least one multi-element transducer includes a plurality of multi-element transducers; and
the processor is configured to calculate a location of a source of the shear horizontal-type acoustic emissions in said structure using a source location algorithm, at least one guided wave velocity in the structure, and the shear horizontal-type and Lamb-type acoustic emission signal data.

9. The system of claim 7, wherein the processor is configured to characterize a source of the at least one shear horizontal-type acoustic emissions based on relative characteristics of the shear horizontal-type acoustic emissions detected by the at least one circumferentially-polarized $d_{15}$ shear ring element and the Lamb-type acoustic emissions detected by the at least one disk-shaped $d_{33}/d_{13}$-type piezoelectric element.

10. A system, comprising:
a plurality of transducers configured to be disposed on a structure, and
a controller electrically coupled to the plurality of transducers, the controller including
a machine-readable storage medium, and
a processor in signal communication with the machine-readable storage medium, the processor configured to
store acoustic emission signal data in the machine-readable storage medium when a signal amplitude detected by at least one of the plurality of transducers crosses a threshold,
cause a pulse generator to pulse at least one of the plurality of transducers to transmit ultrasonic guided wave energy in the structure,
process at least one guided wave signal resulting from said transmitted ultrasonic guided wave energy to identify at least one of a presence, a location, or a severity of at least one defect in the structure, and
store the at least one guided wave signal in the machine-readable storage medium.

11. The system of claim 10, wherein at least one of the plurality of transducers includes a circumferentially-polarized $d_{15}$ shear ring transducer configured to detect and transmit shear horizontal-type guided waves.

12. The system of claim 11, wherein
the at least one circumferentially-polarized $d_{15}$ shear ring transducer includes a plurality of circumferentially-polarized $d_{15}$ shear ring transducers, and
the processor is configured to identify the location of the defect in the structure by one of a synthetic focusing back-propagation algorithm or a computed tomography algorithm.

13. The system of claim 10, wherein at least one of the plurality of transducers includes a magnetostrictive transducer configured to detect and transmit one of shear horizontal-type guided waves or Lamb-type guided waves.

14. The system of claim 13, wherein
the structure includes at least one of a pipe or a tube,
the at least one magnetostrictive transducer includes a plurality of magnetostrictive transducers configured circumferentially around said pipe or said tube, and
the processor is configured to identify the location of the defect in said pipe or said tube using a synthetic focusing back-propagation algorithm.

15. A method, comprising
detecting, using a processor and a plurality of circumferentially-polarized $d_{15}$ shear ring transducers disposed on a structure, a shear horizontal-type acoustic emission in a first frequency band in the structure;
storing shear horizontal-type acoustic emission signal data in a machine-readable storage medium when an amplitude of the shear horizontal-type acoustic emission detected by at least one of the plurality of circumferentially-polarized $d_{15}$ shear ring transducers crosses a first threshold; and calculating, using the processor, a location of a source of the shear horizontal-type acoustic emission in said structure using a source location algorithm, a velocity of the shear horizontal-type acoustic emission in the structure, and the shear horizontal-type acoustic emission signal data.

16. The method of claim 15, further comprising identifying the location of the source of the shear horizontal-type acoustic emission in the structure using a synthetic focusing back-propagation algorithm.

17. The method of claim 15, further comprising
causing, using the processor, a pulse generator to pulse at least one of the plurality of transducers such that ultrasonic guided wave energy is transmitted in the structure;

processing at least one guided wave signal resulting from said transmitted ultrasonic guided wave energy to identify at least one of a presence, a location, or a severity of at least one defect in the structure; and storing the at least one guided wave signal in the machine-readable storage medium.

18. The method of claim 17, wherein the location of the at least one defect in the structure is calculated using one of a synthetic focusing back-propagation algorithm or a computed tomography algorithm.

19. The method of claim 15, further comprising
detecting, using the processor and a plurality of disk-shaped $d_{33}/d_{13}$-type piezoelectric transducers disposed on the structure, a Lamb-type acoustic emission in said structure;

storing Lamb-type acoustic emission signal data in the machine-readable storage medium when an amplitude of the Lamb-type acoustic emission detected by at least one of the plurality of disk-shaped $d_{33}/d_{13}$-type piezoelectric transducers crosses a second threshold, and calculating the location of the source of the acoustic emission in said structure using the source location algorithm, at least one Lamb wave velocity in said structure, and the Lamb-type acoustic emission signal data from the plurality of disk-shaped $d_{33}/d_{13}$-type piezoelectric transducers.

20. The method of claim 19, further comprising characterizing the source of the acoustic emission based on relative characteristics of the shear horizontal-type acoustic emission detected by the plurality of circumferentially-polarized $d_{15}$ shear ring transducers and the Lamb-type acoustic emission detected by the plurality of disk-shaped $d_{33}/d_{13}$-type piezoelectric transducers.

21. The method of claim 15, further comprising
detecting, using the processor and the plurality of circumferentially-polarized $d_{15}$ shear ring transducers disposed on the structure, at least one Lamb-type acoustic emission in a second frequency band in said structure;

storing Lamb-type acoustic emission signal data based on the at least one Lamb-type acoustic emission in the second frequency band in the machine-readable storage medium when an amplitude of the at least one Lamb-type acoustic emission in the second frequency band detected by at least one of the plurality of circumferentially-polarized $d_{15}$ shear ring transducers crosses a second threshold; and calculating the location of the source of the acoustic emission in the structure using a source location algorithm, a velocity of the at least one Lamb-type acoustic emission in the second frequency band, and the Lamb-type acoustic emission signal data.

22. The method of claim 21, further comprising characterizing the source of the acoustic emission based on relative characteristics of the shear horizontal-type acoustic emission and the Lamb-type acoustic emission detected by the plurality of circumferentially-polarized $d_{15}$ shear ring transducers in the first and second frequency bands.

* * * * *